United States Patent
Subramanian et al.

(10) Patent No.: US 12,097,296 B2
(45) Date of Patent: Sep. 24, 2024

(54) SCANNING AND DISINFECTING SYSTEM

(71) Applicant: Goodrich Corporation, Charlotte, ND (US)

(72) Inventors: Sanith Kurumpilavu Subramanian, Bangalore (IN); Raja Mandava, Rammurthy Nagar (IN); Dharamveer Surya Prakash Bathla, Sonipat (IN)

(73) Assignee: Goodrich Corporation, Charlotte, NC (US)

(*) Notice: Subject to any disclaimer, the term of this patent is extended or adjusted under 35 U.S.C. 154(b) by 239 days.

(21) Appl. No.: 17/340,700

(22) Filed: Jun. 7, 2021

(65) Prior Publication Data
US 2022/0001051 A1 Jan. 6, 2022

(30) Foreign Application Priority Data

Jun. 11, 2020 (IN) .............................. 202041024568
Jun. 11, 2020 (IN) .............................. 202041024569

(51) Int. Cl.
*A61L 2/10* (2006.01)
*A61L 2/08* (2006.01)
(Continued)

(52) U.S. Cl.
CPC .................. *A61L 2/10* (2013.01); *A61L 2/085* (2013.01); *A61L 2/24* (2013.01); *B64F 5/30* (2017.01);
(Continued)

(58) Field of Classification Search
CPC ... A61L 2/10; A61L 2/08; A61L 2/085; A61L 2/24; A61L 2202/11; A61L 2202/14; A61L 2202/25; B64F 5/30
See application file for complete search history.

(56) References Cited

U.S. PATENT DOCUMENTS

| 10,500,296 B2 | 12/2019 | Kreitenberg |
| 2016/0213798 A1 | 7/2016 | Paver, Jr. |

(Continued)

FOREIGN PATENT DOCUMENTS

| AU | 2019202299 A1 | 5/2019 |
| CN | 109481708 A | 3/2019 |

(Continued)

OTHER PUBLICATIONS

Extended Search Report for European Application No. 21179094.4 dated Nov. 3, 2021, 10 pages.

*Primary Examiner* — Timothy C Cleveland
(74) *Attorney, Agent, or Firm* — Suiter Swantz IP

(57) ABSTRACT

A disinfection system is disclosed. The disinfection system includes a base, a first arm mechanically coupled to the base at a first joint, a second arm mechanically coupled to the first arm at a second joint, and an emission module mechanically coupled to the second arm at a third joint. The emission module may include a third arm that includes one or more scanners configured to emit electromagnetic energy further configured to disinfect a first surface. The emission module may also include the one or more scanners, focusing lens, a lens frame, and a rotary actuator, wherein the rotary actuator is configured to align one of the one or more scanners with the focusing lens to produce a narrow electromagnetic beam, or position the focusing lens out of alignment with the one of the one or more scanners to produce a broad electromagnetic beam.

8 Claims, 21 Drawing Sheets

(51) Int. Cl.
 *A61L 2/24* (2006.01)
 *B64F 5/30* (2017.01)
(52) U.S. Cl.
 CPC ........ *A61L 2202/11* (2013.01); *A61L 2202/14* (2013.01); *A61L 2202/25* (2013.01)

(56) References Cited

U.S. PATENT DOCUMENTS

| | | |
|---|---|---|
| 2016/0250362 A1 | 9/2016 | MacKin |
| 2016/0271803 A1 | 9/2016 | Stewart |
| 2017/0290935 A1 | 10/2017 | Boodaghians et al. |
| 2018/0193502 A1 | 7/2018 | Ufkes |

FOREIGN PATENT DOCUMENTS

| | | |
|---|---|---|
| CN | 111714654 A | 9/2020 |
| KR | 200463778 Y1 | 11/2012 |
| WO | 2018167760 A3 | 11/2018 |
| WO | 2020060507 A1 | 3/2020 |

SCANNING AND DISINFECTING SYSTEM

PRIORITY

The present application claims the benefit under 35 U.S.C. § 119(e) of Indian Provisional App. No. 202041024568 (filed Jun. 11, 2020), entitled "AIRCRAFT INTERIOR SCANNING AND DISINFECTING SYSTEM FOR ENTIRE AIRCRAFT FLIGHT CYCLE", and Indian Provisional App. No. 202041024569 (filed Jun. 11, 2020), entitled "AIRCRAFT CEILING MOUNTED SCANNING AND DISINFECTING SYSTEM", which are both incorporated herein by reference in its entirety.

BACKGROUND

Interior systems within aircraft or other passenger vehicles consist or seating systems, lavatory systems, entertainments systems, galley systems, galley systems, and various other systems. Each of these systems may be touched by crew or passengers while in use. When one or more passengers or crewmen are infected by a microbe (e.g., virus, bacteria, or fungus), the microbe may be transmitted to any surface of the on-board systems via touch, sneezing, coughing, or other transmission mechanisms. These surfaces may be touched and retained by another person, effectively transmitting the microbe. Current system to disinfect aircraft interiors include manual spraying and wiping surfaces with disinfection solution, a method that is time consuming, and uses toxic materials that may degrade interior surfaces over time. Accordingly, it is desirable to provide a system that avoids the shortcomings of conventional approaches.

SUMMARY

A disinfection system is disclosed. In one or more embodiments, the disinfection system includes a base. In one or more embodiments, the disinfection system further includes a first arm mechanically coupled to the base at a first joint, wherein the first arm is configured to rotate along a first axis. In one or more embodiments, the disinfection system further includes a second arm mechanically coupled to the first arm at a second joint, wherein the second arm is configured to rotate along a second axis. In one or more embodiments, the disinfection system further includes an emission module mechanically coupled to the second arm at a third joint and configured rotate along a third axis comprising one or more scanners wherein the one or more scanners are configured to emit electromagnetic energy upon a first surface, wherein the electromagnetic energy is configured to disinfect the first surface. In one or more embodiments, the disinfection system further includes a sensor configured to detect the presence of a person at the first surface. In one or more embodiments, the disinfection system further includes a first actuator operationally coupled to at least one of the first arm the second arm, or the emission module. In one or more embodiments, the disinfection system further includes a controller communicatively coupled to the emission module, the scanner, and the first actuator. In one or more embodiments, the controller includes at least one processor. In one or more embodiments, the controller further includes a memory coupled to the at least one processor. In one or more embodiments, the memory includes instructions stored upon that, when executed by the at least one processor, causes the controller to determine an absence of a person adjacent to the first surface. In one or more embodiments, the memory includes instructions stored upon that, when executed by the at least one processor, causes the controller to activate at least one of the one or more scanners. In one or more embodiments, the memory includes instructions stored upon that, when executed by the at least one processor, causes the controller to focus the electromagnetic energy on the first surface.

In some embodiments of the disinfection system, the emission module further comprises a swivel block. In some embodiments of the disinfection system, the emission module further comprises at least one third arm coupled to the swivel block at a fourth joint, wherein the at least one third arm is configured to rotate along a fourth axis, wherein the at least one third arm comprises at least one of the one or more scanners.

In some embodiments of the disinfection system, the second arm is configured as a second telescopic arm.

In some embodiments of the disinfection system, the second telescopic arm is configured to rotate along a cylindrical axis.

In some embodiments of the disinfection system, the third arm is configured as a third telescopic arm; wherein the third telescopic arm comprises at least one of the one or more scanners.

In some embodiments of the disinfection system, the third telescopic arm is configured to rotate along a cylindrical axis.

In some embodiments of the disinfection system, the disinfection system further includes comprising a rail slidably coupled to the base.

In some embodiments of the disinfection system, the rail is attached to an interior surface of a vehicle.

In some embodiments of the disinfection system, the emission module further comprises a focusing lens. In some embodiments of the disinfection system, the emission module further comprises a lens frame. In some embodiments of the disinfection system, the emission module further comprises a rotary actuator communicatively coupled to the controller configured to rotate the at least one of the lens frame or at least one of the one or more scanners.

In some embodiments of the disinfection system, the base is configured to attach to a passenger seat.

In some embodiments of the disinfection system, the electromagnetic energy is configured as at least one of ultraviolet light or infrared light.

In some embodiments of the disinfection system, the sensor is configured as a motion sensor.

In some embodiments of the disinfection system, the sensor is configured as a heat sensor.

In some embodiments of the disinfection system, the base further comprises at least one of the one or more scanners.

In some embodiments of the disinfection system the rotary actuator is configured to align the focusing lens with the one of the one or more scanners, wherein the electromagnetic energy is emitted from the one of the one or more scanners as a narrowly focused beam. In some embodiments of the disinfection system, the rotary actuator is configured to position the focusing lens out of alignment with the one of the one or more scanners, wherein the electromagnetic energy is emitted from the one of the one or more scanners as a broadly focused beam.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims. In the drawings:

DETAILED DESCRIPTION

Figure 1:
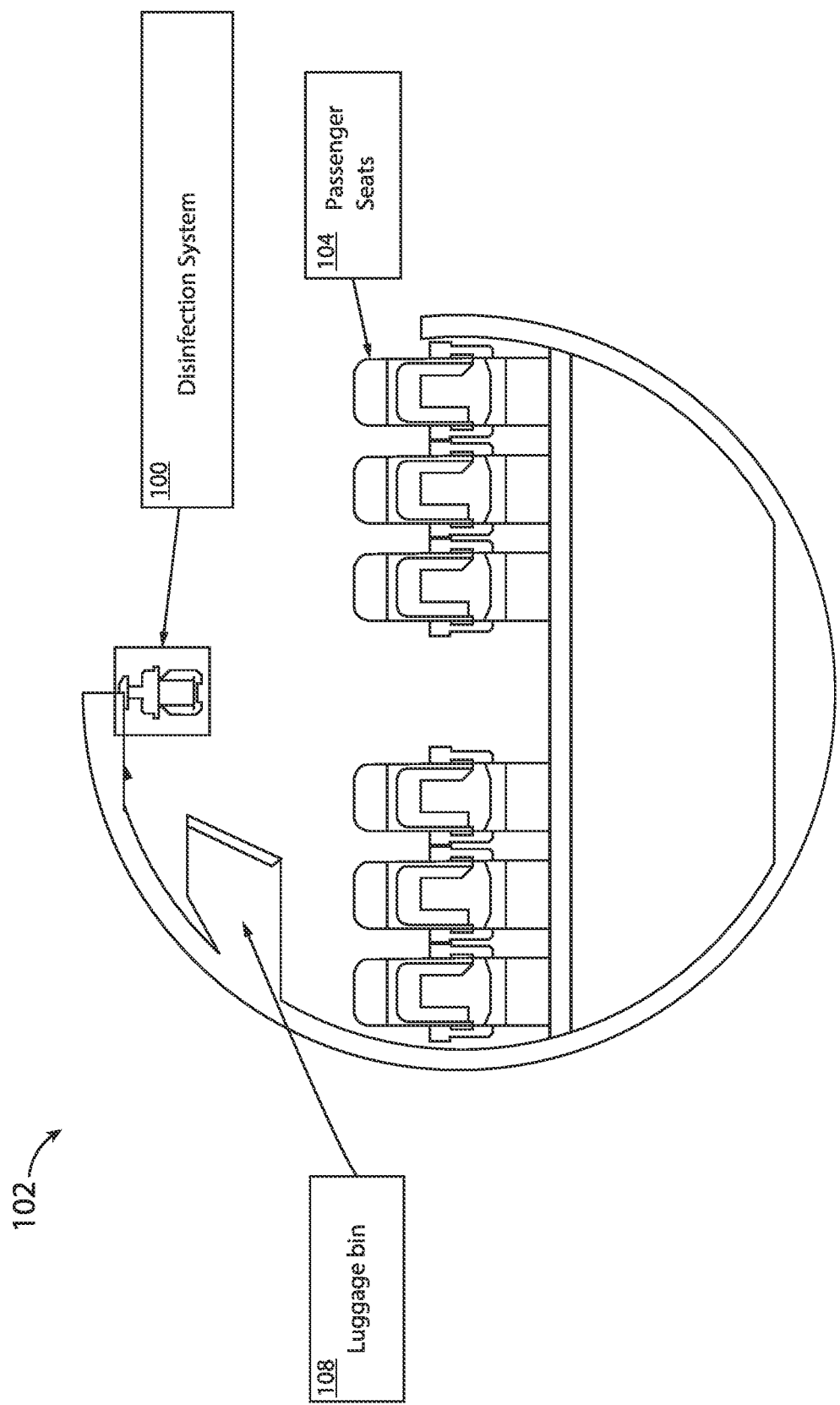
FIG. 1 is a diagram of a cross-section of a disinfection system attached to an interior cabin ceiling of an aircraft, in accordance with one or more embodiments of the disclosure.

Before explaining one or more embodiments of the disclosure in detail, it is to be understood that the embodiments are not limited in their application to the details of construction and the arrangement of the components or steps or methodologies set forth in the following description or illustrated in the drawings. In the following detailed description of embodiments, numerous specific details may be set forth in order to provide a more thorough understanding of the disclosure. However, it will be apparent to one of ordinary skill in the art having the benefit of the instant disclosure that the embodiments disclosed herein may be practiced without some of these specific details. In other instances, well-known features may not be described in detail to avoid unnecessarily complicating the instant disclosure.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Further, unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination of or sub-combination of two or more such features, along with any other features which may not necessarily be expressly described or inherently present in the instant disclosure.

Finally, as used herein any reference to "one embodiment" or "some embodiments" means that a particular element, feature, structure, or characteristic described in connection with the embodiment is included in at least one embodiment disclosed herein. The appearances of the phrase "in some embodiments" in various places in the specification are not necessarily all referring to the same embodiment, and embodiments may include one or more of the features expressly described or inherently present herein, or any combination of sub-combination of two or more such features, along with any other features which may not necessarily be expressly described or inherently present in the instant disclosure.

A disinfection system for interiors, such as vehicle interiors, is disclosed. The disinfection system uses electromagnetic energy to kill and/or sterilize microbes on surfaces, such as passenger seats. The disinfection system includes motion or temperature sensors to detect the presence of people, which upon detection of people, the system will turn off, or otherwise prevent the electromagnetic energy from reaching the people. The disinfection system also includes a framework of actuators, arms, and other mechanical and software componentry that enable the disinfection system to intelligently and efficiently disinfect interior surfaces.

FIG. 1 is a diagram of a cross-section of a disinfection system 100 attached to an interior cabin ceiling of an aircraft 102, in accordance with one or more embodiments of the disclosure. The disinfection system 100 may be disposed within any vehicle or building including but not limited the interior surfaces of aircraft 102, busses, trains, movie theatres, conference areas, kitchens, and waiting rooms. For example, the disinfection system 100 may be attached to the ceiling of a passenger aircraft.

Figure 2:
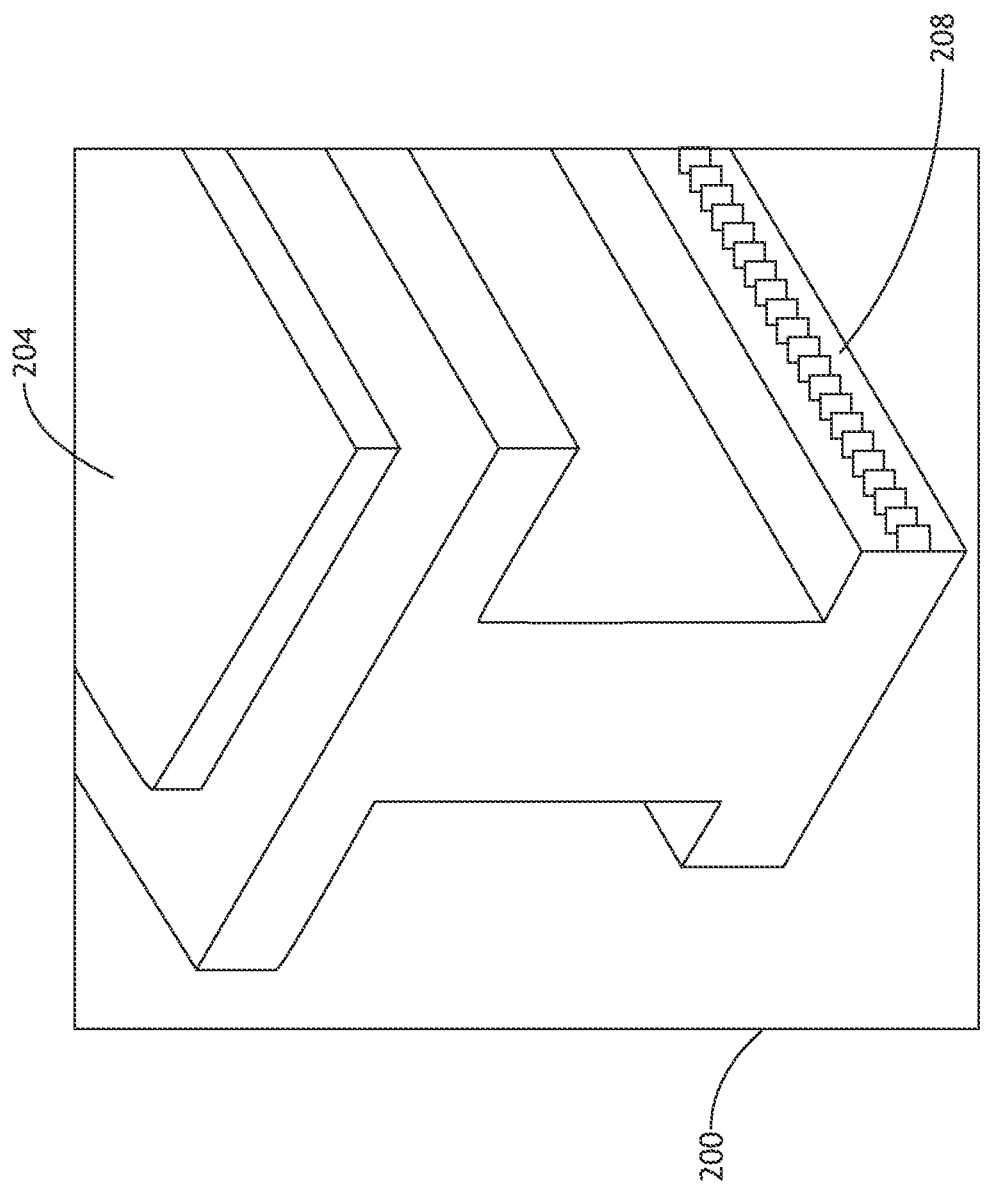
FIG. 2 is a diagram illustrating a perspective view of a section of a rail configured for transporting the disinfection system, in accordance with one or more embodiments of the disclosure.

In some embodiments, the disinfection system 100 is attached to an interior surface via a rail, as partially illustrated in a perspective view in FIG. 2. The rail 200 both tethers componentry of the disinfection system 100 to an interior surface (e.g., the ceiling of the aircraft 102), and allows the componentry of the disinfection system 100 to slide along the rail 200. The rail 200 includes an attachment surface 204 configured to attach the rail 200 to the interior surface. The attachment surface 204 may utilize any technology for attaching rail to the interior surface. For example, the attachment surface may be configured as an adhesive strip that bonds the rails 200 to the interior surface of an aircraft cabin. In another example, the attachment surface 204 may be configured as an attachment plate that bolts to a ceiling. In some embodiments, the rail 200 further includes a rack 208 configured with teeth to mechanically interact with gearing from the disinfection system 100.

In some embodiments, the disinfection system 100 is attached to an interior surface via a rail, as partially illustrated in a perspective view in FIG. 2. The rail 200 both tethers componentry of the disinfection system 100 to an interior surface (e.g., the ceiling of the aircraft 102), and allow the componentry of the disinfection system 100 to slide along the rail 200. The rail 200 includes an attachment surface 204 configured to attach the rail 200 to the interior surface. The attachment surface 204 may utilize any technology for attaching rail to the interior surface. For example, the attachment surface may be configured as an adhesive strip that bonds the rails 200 to the interior surface of an aircraft cabin. In another example, the attachment surface 204 may be configured as an attachment plate that bolts to a ceiling. In some embodiments, the rail 200 further includes a rack 230 configured to with teeth mechanically interact with gearing from the disinfection system 100.

Figure 3:
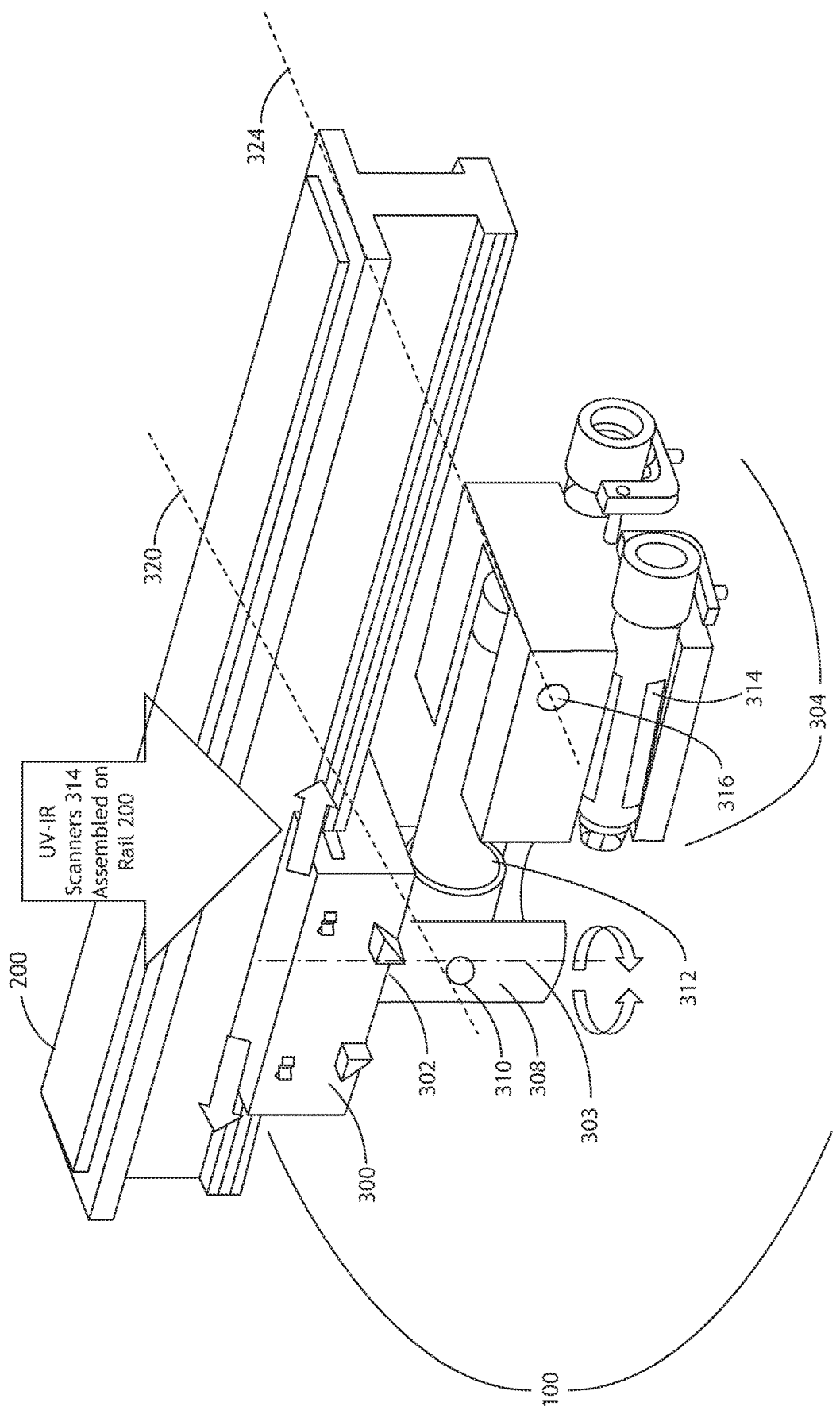
FIG. 3 is a perspective view of the disinfection system attached to a rail, in accordance with one or more embodiments of the disclosure.

FIG. 3 is a perspective view of the disinfection system 100 attached to the rail, in accordance with one or more embodiments of the disclosure. In some embodiments, the disinfection system includes a base 300 configured to slidably attach the disinfection system 100 to the rail 200. The disinfection system further includes an emission module 304. The emission module 304 is attached to the base 300 via a first arm 308 and a second arm 312. The first arm 308 is mechanically coupled to the base 300 at a first joint 302 and configured to rotate along a first axis 303. The first axis 303 may be configured as an axis relative to any plane of the attachment surface 204 of the rail 200. For example, the first axis 303 may be approximately perpendicular to the plane of the attachment surface 204 of the rail 200. The emission module 304 further includes one or more scanners 314 configured to emit electromagnetic energy (e.g., ultraviolet light or infrared light).

The second arm 312 is mechanically coupled to the first arm 308 at a second joint 310 and to the emission module 304 at a third joint 316. The second arm 312 is configured to rotate along a second axis 320 relative to any plane of the attachment surface 204 of the rail 200. For example, the second axis 320 may be configured as approximately parallel to the attachment surface 204 of the rail 200. The emission module 304 is configured to rotate along a third axis 324 relative to any plane of the attachment surface 204 of the rail 200. For example, the second axis 324 may be configured as approximately parallel to the attachment surface 204 of the rail 200.

It is to be understood that the first axis 303, second axis 320, third axis 324, and any subsequent axes of rotation within components of the disinfection system 100 may have any orientation in relationship from each other, and one or more axes may be identical depending on the positioning of the emission module. Importantly, the disinfection system 100 is configured with multiple degrees of freedom that (e.g., via the first joint 302, second joint 310, and third joint 3161, allow the emission module to be freely arranged in many different positions. The first joint 302, second joint 310, and/or third joint 316 may be configured with any type of mechanical joint that allows rotation along one of more degrees of freedom between two bodies including but not limited to a pin joint, a ball joint, a knuckle joint, a turnbuckle, a cotter joint, a bolted, joint, a screw joint, or a universal joint. The first joint 302, second joint 310, and/or third joint 316 may be articulated manually and/or by any actuating technology.

Figure 4:
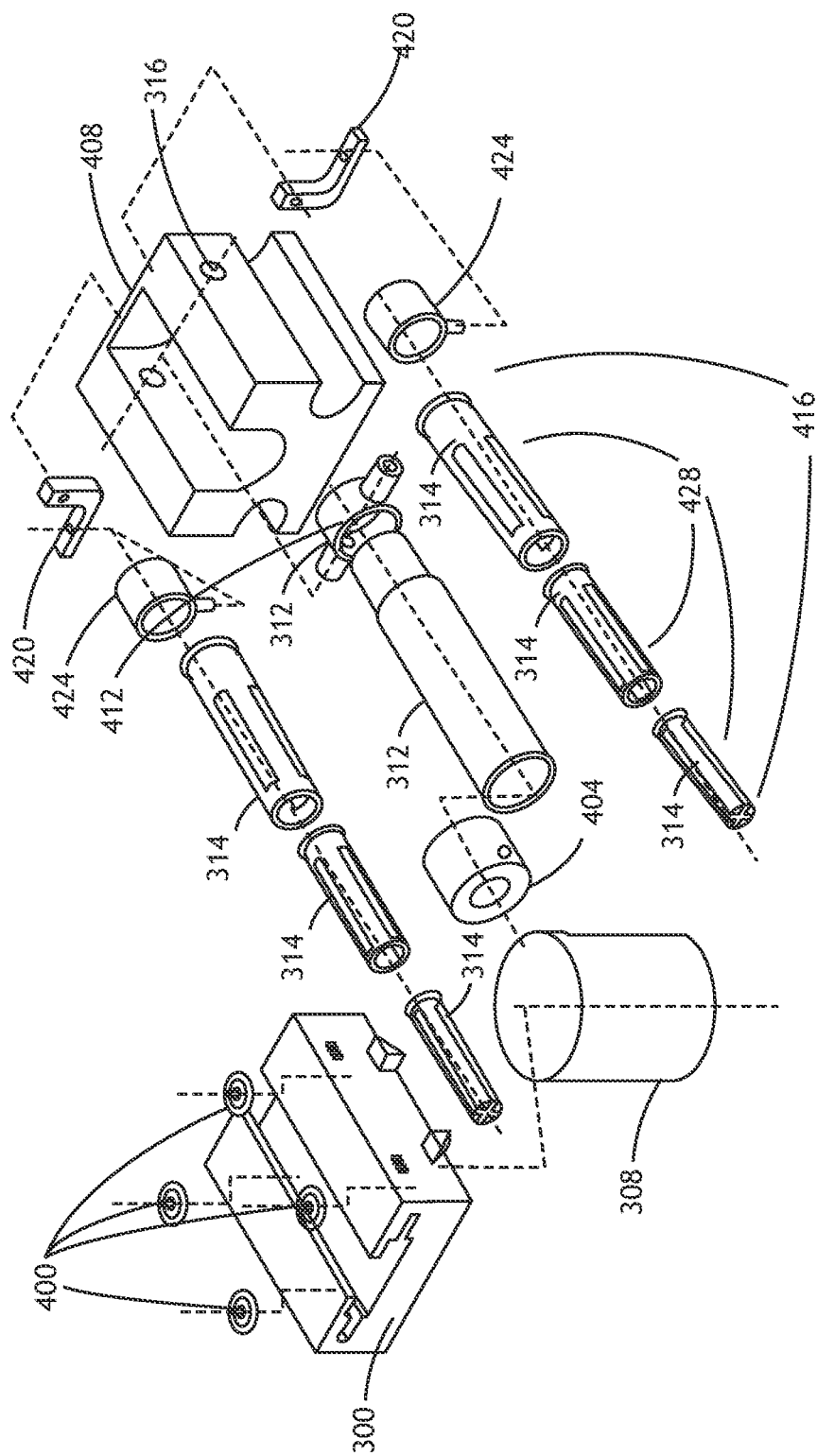
FIG. 4 illustrates an exploded view of the disinfection system, in accordance with one or more embodiments of the disclosure.

FIG. 4 illustrates an exploded view of the disinfection system 100, in accordance with one or more embodiments of the disclosure. The base 300 includes one or more pinion gears 400 that mesh with the rack 208. The first arm 308 is coupled underneath the base 300 (e.g., on the surface opposite of the surface interacting with the rail 200) and is coupled to the second arm 312.

FIG. 4 illustrates an exploded view of the disinfection system 100, in accordance with one or more embodiments of the disclosure. The base 300 includes one or more pinion gears 400 that mesh with the rack 230. The first arm 308 is coupled underneath the base 300 (e.g., on the surface opposite of the surface interacting with the rail 200) and is coupled to the second arm 312.

In some embodiments, the disinfection system 100 includes a first actuator 404 operating at the interface between the first arm 308 and the second arm 312 (e.g., at the second joint 310). The first actuator 404 may be configured as any type of moving and controlling mechanism including but not limited to a rotary actuator or servomotor. The second arm 312 may be configured as a second telescoping arm. For example, the second arm 312 may be configured as an automated two-element telescopic arm (e.g., operated via a linear activator) that can extend to approximately twice the length of the retracted second 312 arm. The second arm may also include a first telescoping clamp configured to prevent the telescoping arm from prematurely extending and/or preventing rotational movement of the first arm 308 and/or second arm 312.

The second arm is coupled to the emission module 304 via a swivel block 408 at third joint 316. Motion of the swivel block 408 relative to the second arm 312 may be controlled via a second actuator 412 operating at the third joint 316. The second actuator 412 may be configured as any type of moving and controlling mechanism as described herein.

The one or more scanners 314 are disposed upon a third arm 416 mechanically coupled to the swivel block 408. The third arm 416 may be attached to the swivel block 408 via a block clamp 420 configured to allow for rotation of the third arm 416 via a third actuator 424. The third arm 416 may be configured as a third telescopic arm, comprised of two of more telescopic sections 428. One or more of the telescopic sections 428 may include one or more of the one or more scanners 314 (e.g., located on the side of each telescopic sections or on the cylindrical face of the terminal telescopic section). The telescopic sections 428 may be extended and retracted via a linear activator. The third arm may also include a second telescoping clamp configured to prevent the one or more telescopic sections 428 from prematurely extending.

Figure 5:
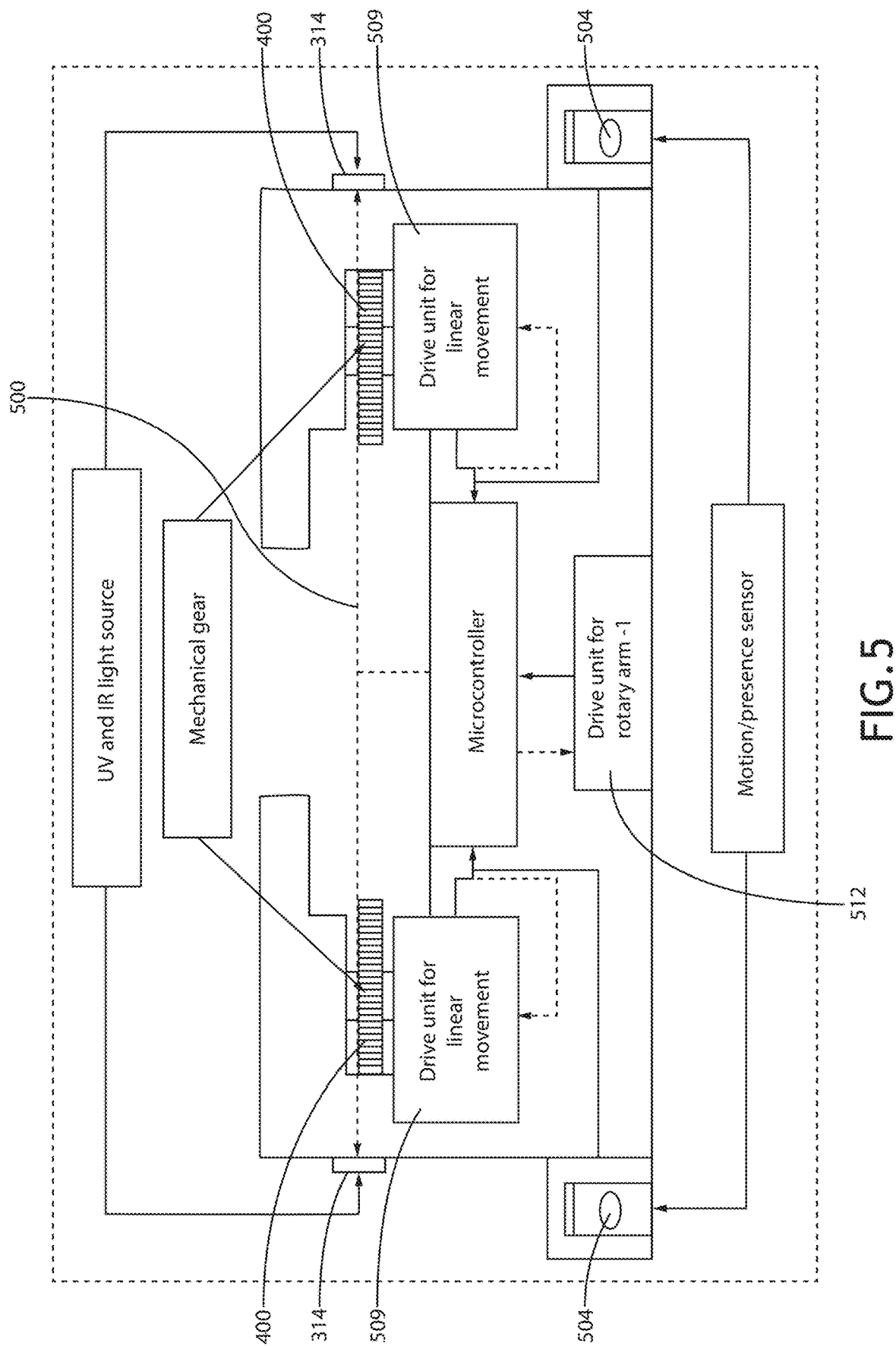
FIG. 5 illustrates a close-up, cross-section view of the base, in accordance with one or more embodiments of the disclosure.

FIG. 5 illustrates a close-up, cross-section view of the base 300, in accordance with one or more embodiments of the disclosure. The base 300 includes a track groove 500 that receives the rail 200, and facilitates the alignment of the pinion gears 400. The base 300 may include one or more scanners 314 (e.g., to disinfect the ceiling and/or the one or more luggage bins 108). The base 300 may also include one or more sensors 504 configured to detect the presence or absence of a person (e.g., a passenger). The sensor may 504 include any type of sensor 504 including but not limited to a motion sensor and a heat sensor. The base 300 may include a fourth actuator 509 configured to drive the pinion gears 400. The base may also include a fifth actuator 512 configured to rotate the first arm 308. The many actuators, sensors, and scanners 314 of the disinfection system 100 may be controlled via a controller 508 configured to provide processing functionality for the disinfection system 100.

Figure 6A:
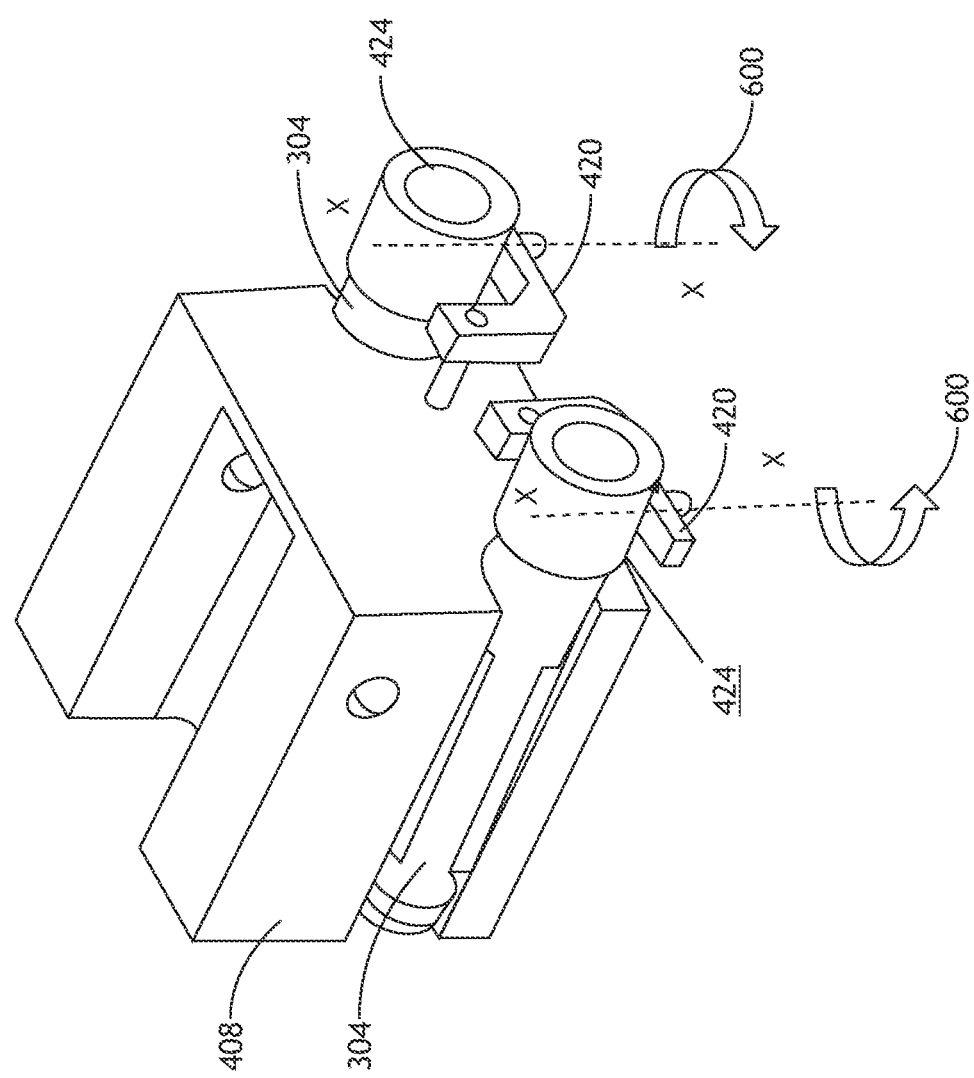
FIG. 6A is a close-up view of the emission module configured with the third arm in a folded and retracted position, in accordance with one or more embodiments of the disclosure.
Figure 6B:
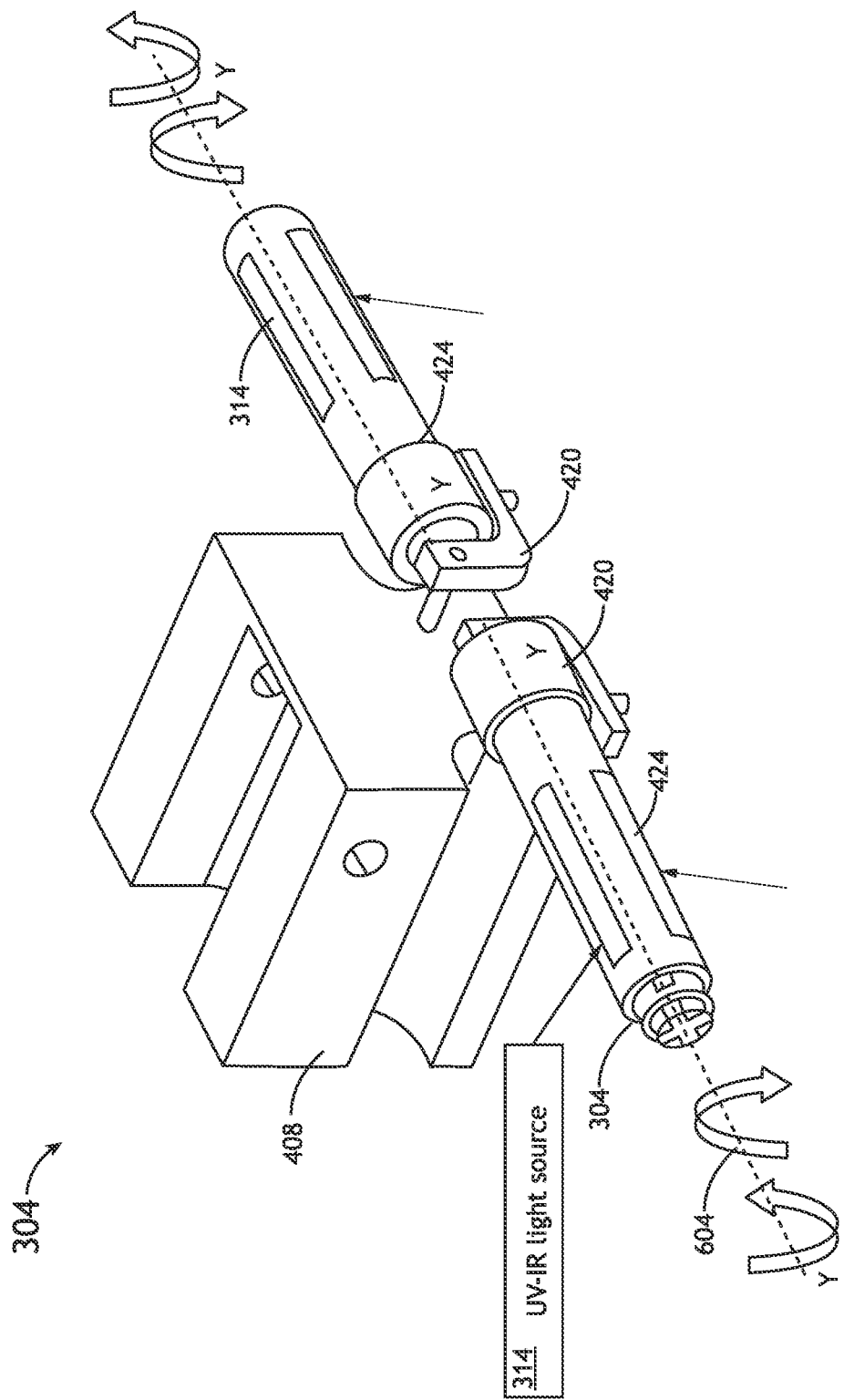
FIG. 6B is a close-up view of the emission module configured with the third arm in an unfolded and retracted position, in accordance with one or more embodiments of the disclosure.
Figure 6C:
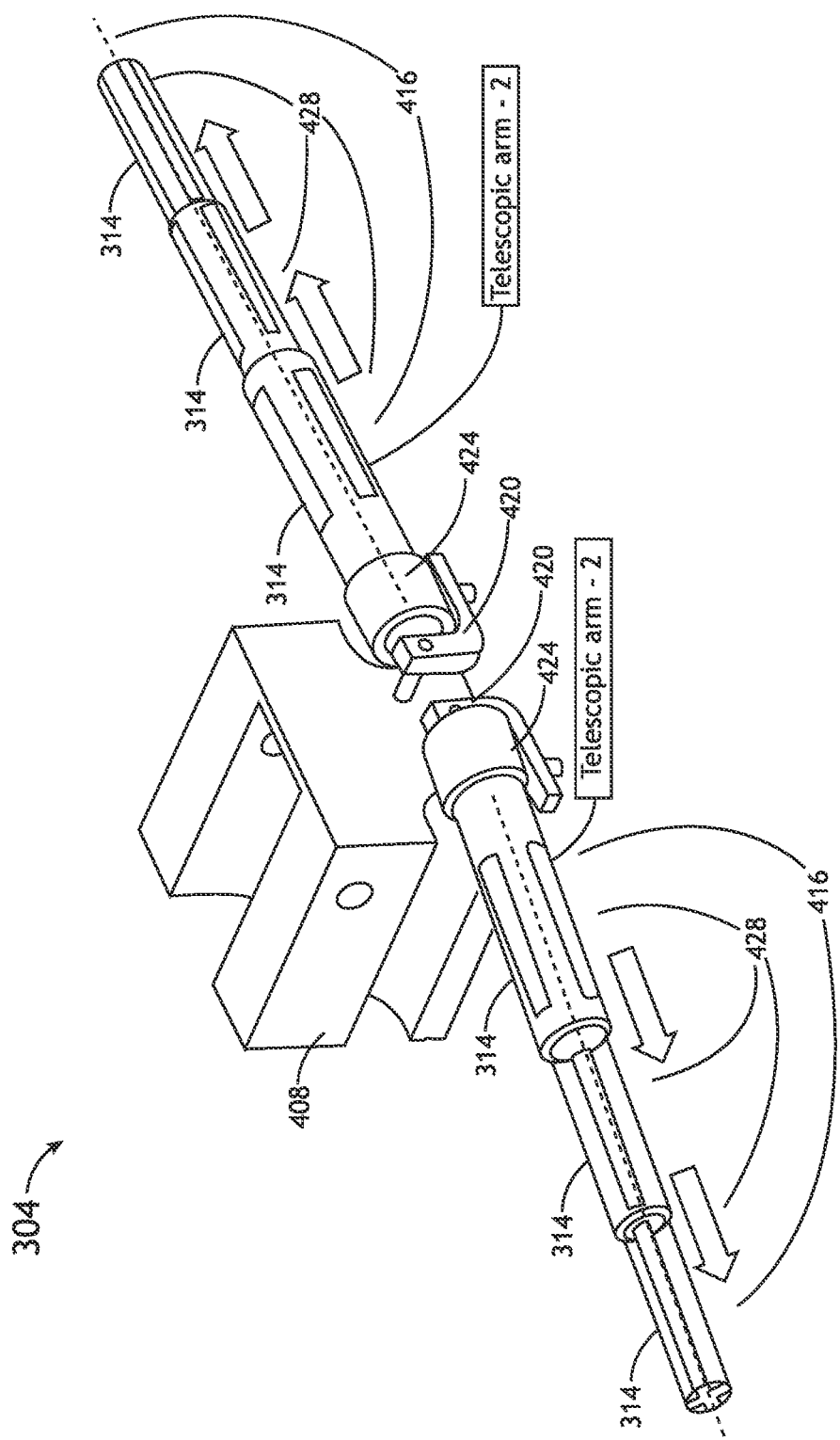
FIG. 6C is a close-up view of the emission module configured with the third arm in an unfolded and extended position, in accordance with one or more embodiments of the disclosure.

FIG. 6A is a close-up view of the emission module 304 configured with the third arm 416 in a folded and retracted position, in accordance with one or more embodiments of the disclosure. The third arms 416 are retracted and folding within grooves built into the body of the swivel block 408 via the third actuators 424 (e.g., a swing-out motion 600 the point of rotation occurring at the block clamps 420). Upon unfolding of the third arms 416 (e.g., as shown in FIG. 6B), the third arms 416 are capable of rotation along a cylindrical axis (e.g., a fourth axis 604), which adjust the position of the scanners 314 via either the third actuator 424 or a sixth actuator. The third arms 416 may also extend, via the telescopic sections 428, increasing the number of scanners 314 that can be used to scan surfaces (e.g., as shown in FIG. 6C).

FIG. 6A is a close-up view of the emission module 304 configured with the third arm 416 in a folded and retracted position, in accordance with one or more embodiments of the disclosure. The third arms 416 are retracted and folding within grooves built into the body of the swivel block 408 via the third actuators 424 (e.g., a swing-out motion 600 the point of rotation occurring at the block clamps 420). Upon unfolding of the third arms 304 (e.g., as shown in FIG. 6B), the third arms 304 are capable of rotation along a cylindrical axis (e.g., a fourth axis 604), which adjust the position of the scanners 314 via either the third actuator 424 or a sixth actuator. The third arms 416 may also extend, via the telescopic sections 428, increasing the number of scanners 314 than can be used to scan surfaces (e.g., as shown in FIG. 6C).

Figure 7:
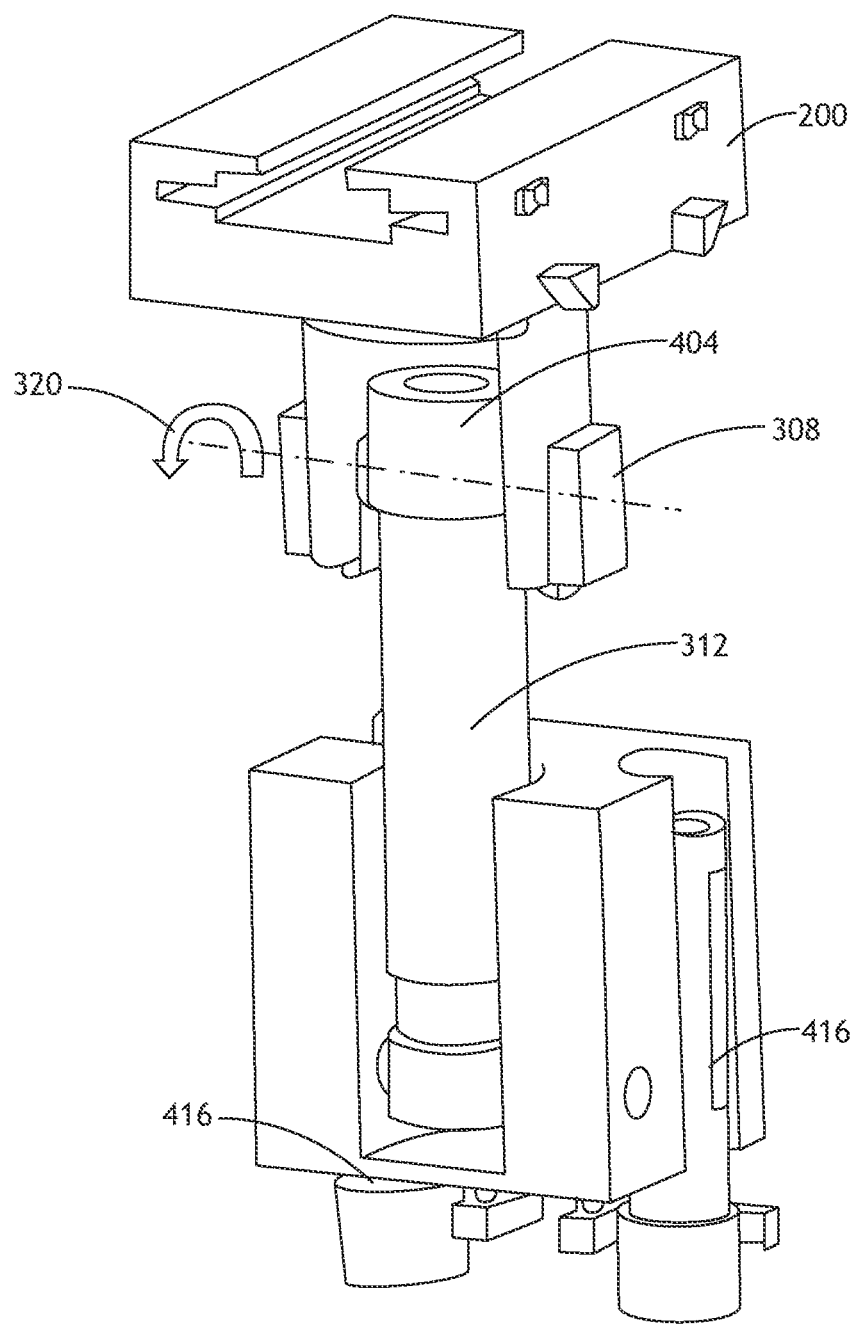
FIG. 7 is a close-up view of the disinfection system configured in an unfolded and retracted position, in accordance with one or more embodiments of the disclosure.
Figure 8:
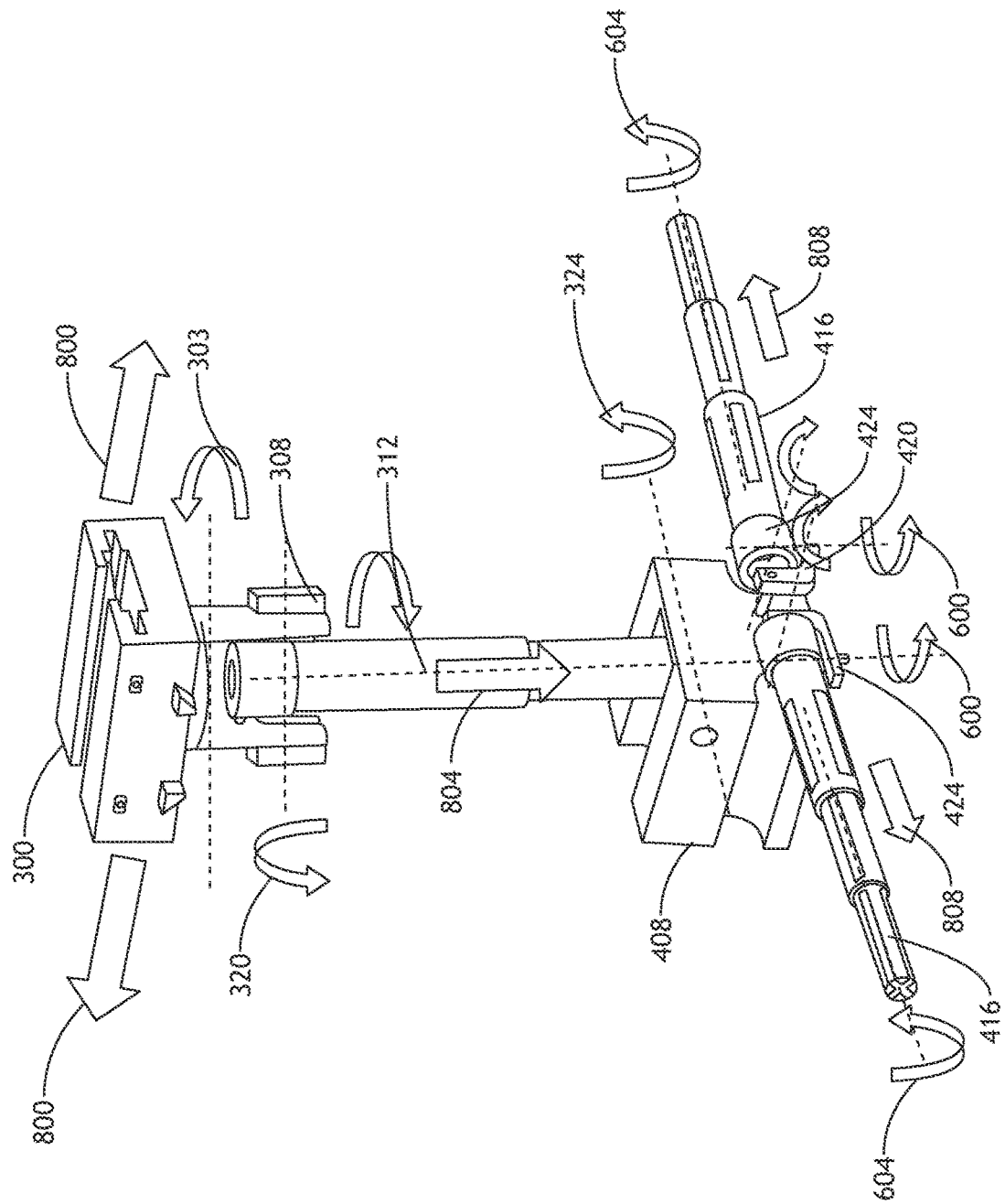
FIG. 8 illustrates a diagram summarizing the movements by the components of the disinfection system, in accordance with one or more embodiments of the disclosure.

FIG. 7 is a close-up view of the disinfection system 100 configured in an unfolded and retracted position, in accordance with one or more embodiments of the disclosure. The second arm 312 has rotated along the second axis 320 via the first actuator 404 from a folded position (e.g., the first arm 308 approximately perpendicular to the second arm 304) to an unfolded position (e.g., the first arm 308 approximately parallel to the second arm 304). Upon rotation of the second arm 312, the third arms 416 may be unfolded and extended.

Figure 9:
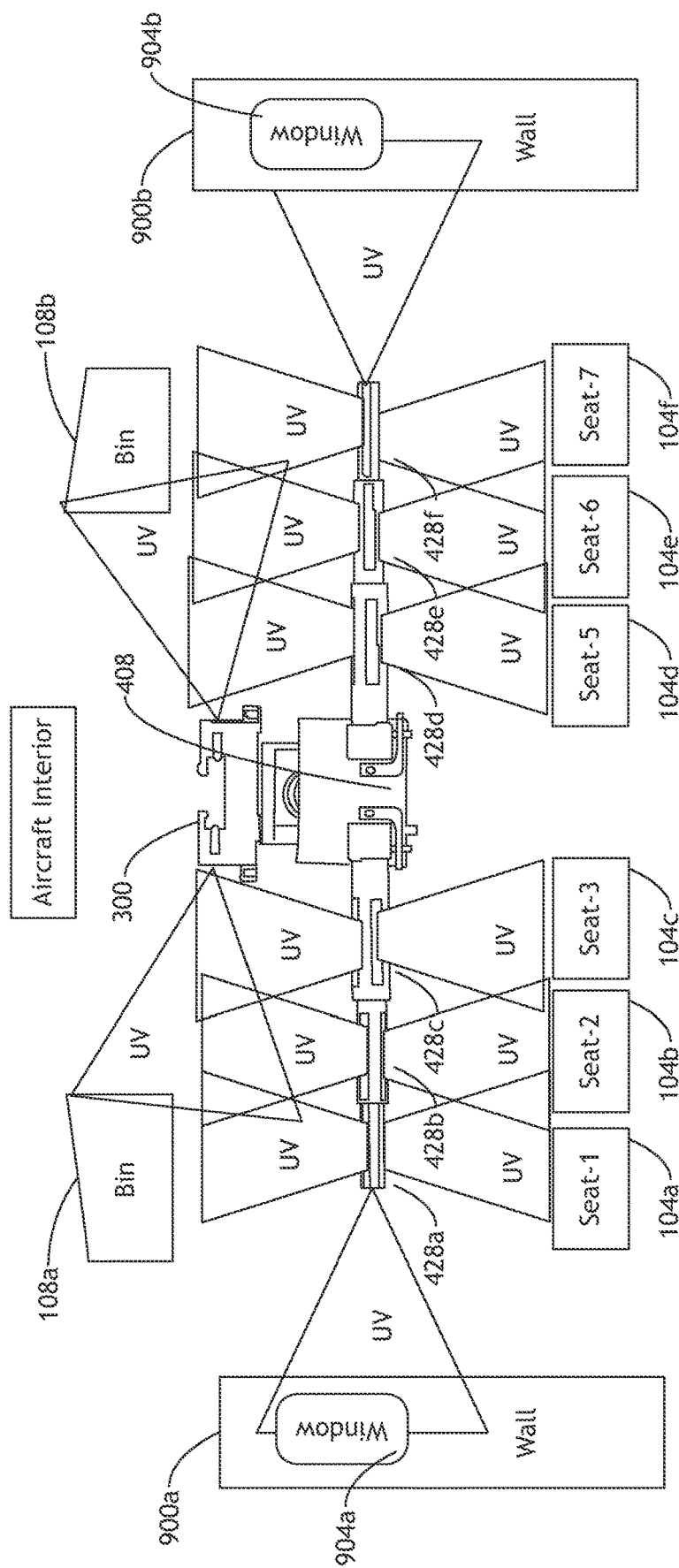
FIG. 9 illustrates a diagram summarizing electromagnetic scanning by the disinfection system within an aircraft, in accordance with one or more embodiments of the disclosure.

FIG. 9 illustrates a diagram summarizing electromagnetic scanning by the disinfection system 100 within an aircraft 102, in accordance with one or more embodiments of the disclosure. The shaded areas represent the scanning of electromagnetic energy (e.g., ultraviolet light) by a plurality of scanners 314 on surfaces (e.g., a first surface) of the aircraft interior. For example, passenger seats 104a-f may be scanned by scanners located on telescopic sections 428a-f, respectively. In another example, over-head bins 108a-b may be scanned by scanners 314 located on the base 300. In another example, walls 900a-b and/or windows 904a-b may be scanned by scanners located on the face of the terminal telescopic sections 428a,f, respectively. The disinfection system 100 may include any configuration and any number of components. Therefore, the above description and illustration should not be construed as limiting the scope of the invention.

FIG. 9 illustrates a diagram summarizing electromagnetic scanning by the disinfection system 100 within an aircraft 102, in accordance with one or more embodiments of the disclosure. The shaded areas represent the scanning of electromagnetic energy (e.g., ultraviolet light) by a plurality of scanners 314 on surfaces (e.g., a first surface) of the aircraft interior. For example, passenger seats 104a-f may be scanned by scanners located on telescopic sections 428a-f, respectively. In another example, over-head bins 108a-b may be scanned by scanners 3014 located on the base 300. In another example, walls 900a-b and/or windows 904a-b may be scanned by scanners located on the face of the terminal telescopic sections 428a,f, respectively. The disinfection system 100 may include any configuration and any number of components. Therefore, the above description and illustration should not be construed as limiting the scope of the invention.

Figure 10:
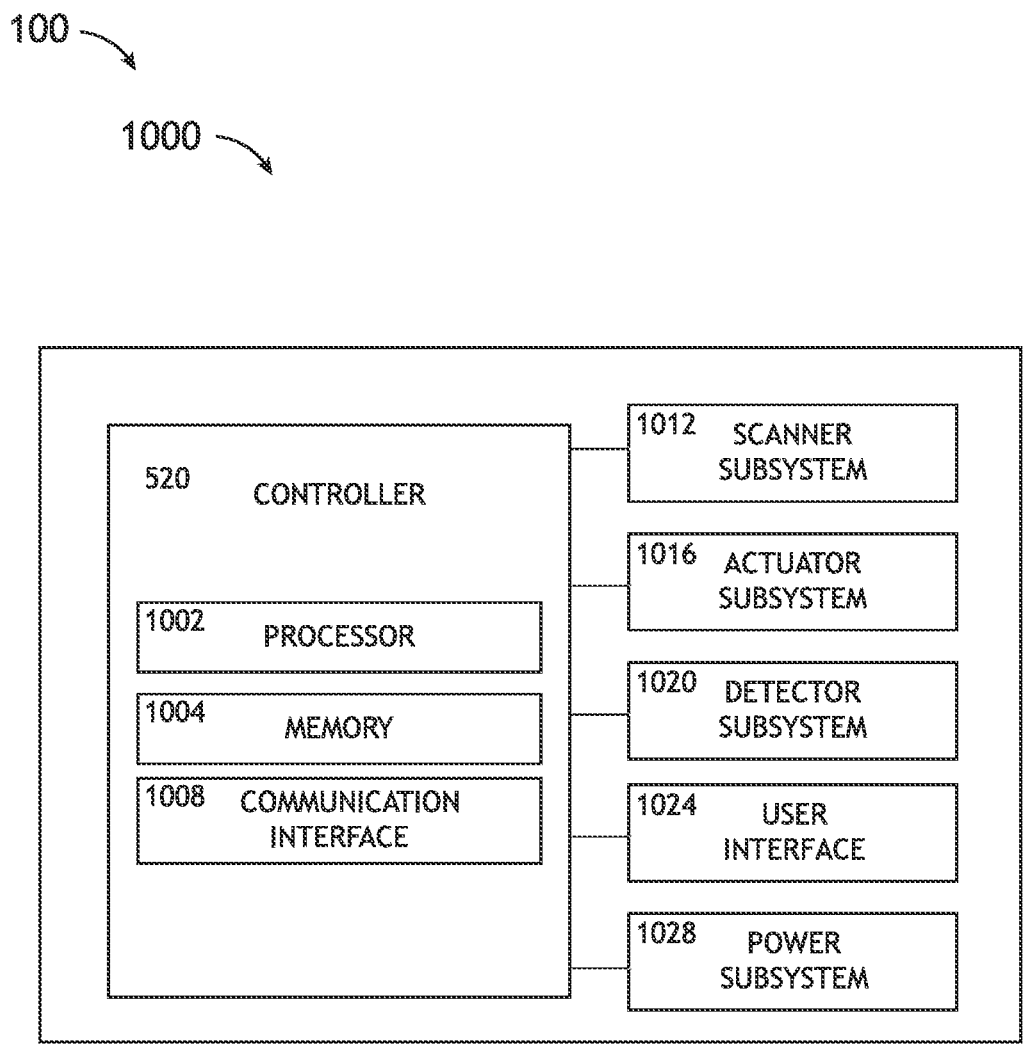
FIG. 10 is a block diagram illustrating a control system of the disinfection system, in accordance with one or more embodiments of the disclosure.

FIG. 10 is a block diagram illustrating a control system 1000 of the disinfection system 100, in accordance with one or more embodiments of the disclosure. The control system 1000 is configured to provide processing functionality for the disinfection system 100, and to interface with componentry within the disinfection system 100. The control system 1000 include the controller 508, which further includes one or more processors 1002 (e.g., micro-controllers, circuitry, integrated circuits, field programmable gate arrays (FPGA), or other processing systems), and resident or external memory 1004 for storing data, executable code, instructions, and other information. The controller 508 can execute one or more software programs embodied in a non-transitory computer readable medium (e.g., memory 1004) that implement techniques described herein (e.g., causing the controller to implement techniques described herein). The controller 508 is not limited by the materials from which it is formed or the processing mechanisms employed therein and, as such, can be implemented via semiconductor(s) and/or transistors (e.g., using electronic integrated circuit (IC) components), and so forth.

The memory 1004 can be an example of tangible, computer-readable storage medium that provides storage functionality to store various data and/or program code associated with operation of the controller 508, such as software programs and/or code segments, or other data to instruct the controller 508, and possibly other components of the disinfection system 100, to perform the functionality described herein. Thus, the memory 1004 can store data, such as a program of instructions for operating the disinfection system 100, including its components (e.g., controller 508), and so forth. It should be noted that while a single memory 1004 is described, a wide variety of types and combinations of memory 1004 (e.g., tangible, non-transitory memory) can be employed. The memory 1004 can be integral with the controller 508, can comprise stand-alone memory, or can be a combination of both. Some examples of the memory 1004 can include removable and non-removable memory components, such as random-access memory (RAM), read-only memory (ROM), flash memory (e.g., a secure digital (SD) memory card, a mini-SD memory card, and/or a micro-SD memory card), solid-state drive (SSD) memory, magnetic memory, optical memory, universal serial bus (USB) memory devices, hard disk memory, external memory, and so forth.

The controller 520 100 further includes a communication interface 1008. The communication interface 1008 can be operatively configured to communicate with components of the disinfection system 100. For example, the communication interface 1008 can be configured to retrieve data from the controller 508 or other components, transmit data for storage in the memory 1004, retrieve data from storage in the memory 1004, and so forth. The communication interface 1008 can also be communicatively coupled with the controller 508 to facilitate data transfer between components of the disinfection system 100. It should be noted that while the communication interface 1008 is described as a component of the controller 508, one or more components of the communication interface 1008 can be implemented as external components communicatively coupled to the controller 508 via a wired and/or wireless connection.

The control system 1000 further includes a scanner subsystem 1012 communicatively coupled to the controller 508 configured to transfer data and/or signals between one or more scanners 314 and the controller 508. The control system 1000 further includes an actuator subsystem 1016 communicatively coupled to the controller 508 configured to transfer data and/or signals between one or more actuators (e.g., first actuator 404, second actuator 412, or extension/retraction actuators) and the controller 508. The control system 1000 further includes a sensor subsystem 1020 communicatively coupled to the controller 508 configured to transfer data and/or signals between one or more sensors (e.g., infrared sensor or heat sensor) and the controller 508.

The control system 1000 further includes a user interface 1024 configured communicatively coupled to the controller 508. The user interface 1024 may include any technology that can receive input and/or transmit output to a user including but not limited to switches, button, displays, touch displays, or keyboards. The user interface may also be configured as a wirelines or wireless interface utilizing waveforms including but not limited to wi-fi, Bluetooth, and 5G. For example, a flight attendant may interact with the disinfection system 100 via a mobile device (e.g., a smart phone) connected by Bluetooth technology.

The control system 1000 further includes a power subsystem 1028 communicatively coupled to the controller 508 configured to manage electrical power for the disinfection system 100. For example, the power subsystem 1028 may harness and manage electrical power from an aircraft main electrical system. In another example, the power subsystem 1028 may manage power from an internal or external battery.

Figure 11:
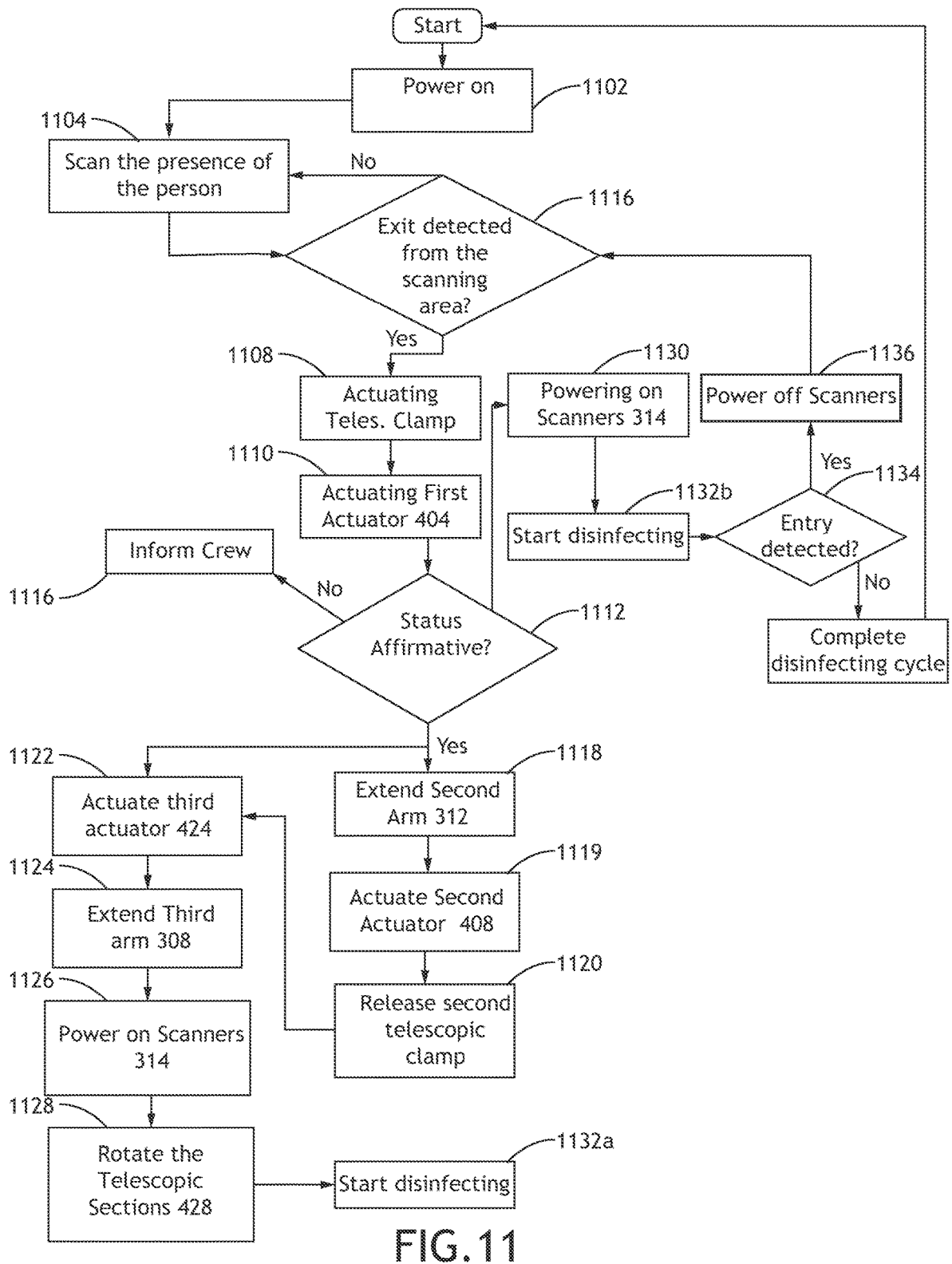
FIG. 11 is a flow chart illustrating a method of operating the disinfection system, in accordance with one or more embodiments of the disclosure.

FIG. 11 is a flow chart illustrating a method 1100 of operating the disinfection system 100, in accordance with one or more embodiments of the disclosure. Once the disinfection system 100 is powered on (e.g., step 1102), a step 1104 of determining the presence or absence of a person in the scanning area is performed. The disinfection system 100 may then perform a step 1106 of determining if all people have exited the scanned area. Once the disinfection system 100 has determined that no person is in the scanning area, a step 1108 of actuating the first telescopic clamp in order to release the telescoping mechanism and/or the first actuator is performed as well as a step 1110 of actuating the first actuator 404.

At one or points in the method 1100, the method will include one or more steps 1112 of checking the operational status (e.g. affirmative or on-line) of the disinfection system 100. For example, if the first actuator of step 110 is unable to actuate, the disinfection system 100 may perform a step 1114 of informing the crew of the error (e.g., via the user interface 1024), for which the crew and/or disinfection system 100 may perform a maintenance step 1116. If the operational status does not indicate an error, the disinfection system 100 may then progress through step 1118 of extending the second arm 312, step 1119 of actuating the second actuator 408, and step 1120 of releasing the second telescopic clamp. The disinfection system 100 may further progress through step 1122 of actuating the third actuator 424, step 1124 of extending the third arm 308 (e.g., by extending the telescopic sections 428), step 1126 of powering on the scanners 314 (e.g., ultraviolet-emitting diodes), and a step 1128 of rotating the telescopic sections 428 of the third arm 308. The disinfection system may 100 also perform a step 1130 of powering on the scanners 314 located on the base 300. Step 1130 may be performed separately, or in concert with, step 1126.

One the scanners 314 have been powered on and are in the correct position, the method 1100 may further progress through a step 1130a, 1130b of initiating the disinfection cycle. While the disinfection system 100 is actively disinfecting, the method 1100 may further progress to a step 1134 of determining if a person has entered the scanning area (e.g., via the one or more sensors 504). If the one or more sensors detect the entry of a person (e.g., or other living entity) into the scanning area, the method 1100 may progress through a step 1136 of powering off the scanners 314. If no entry into the scanning area is determined, the method 110 may further progress to step 1138 of completing the disinfection cycle.

Figure 12:
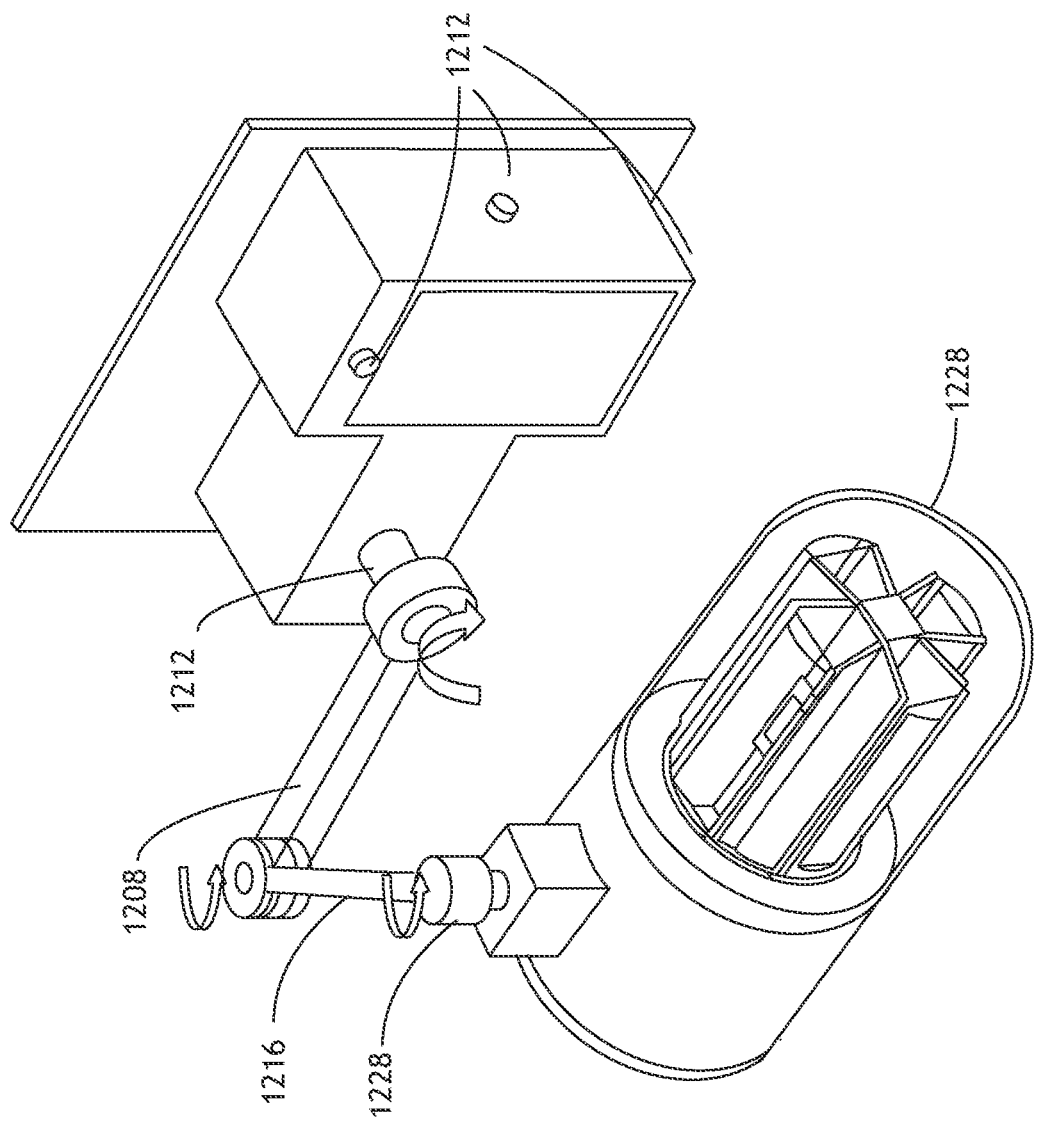
FIG. 12 is a diagram illustrating a disinfection system, in accordance with one or more embodiments of the disclosure.

FIG. 12 is a diagram illustrating a disinfection system 1200, in accordance with one or more embodiments of the disclosure. The disinfection system 1200 may contain one or more, or all, components of disinfection system 1200, and vice versa. Disinfection system 1200 includes a base 1204 configured to attach (e.g., via bolts, adhesive, vacuum pods, or other attachment technology) to an interior surface, such as a passenger seat 104 or the ceiling of an aircraft 102. Disinfection system 1200 further contains a first arm 1208 mechanically coupled to the base 1204 via a first joint 1212. Disinfection system 1200 further includes a second arm 1216 mechanically coupled to the first arm 1208 via a second joint 1220. Disinfection system 1200 further includes an emission module 1224 configured to emit electromagnetic energy (e.g., ultraviolet light or infrared light) mechanically coupled to the second arm 1216 via a third joint 1228.

The first joint 1212, second joint 1220, and/or third joint 1228 may be configured of any type of mechanical joint that allows rotation along one of more degrees of freedom between two bodies including but not limited to a pin joint, a ball joint, a knuckle joint, a turnbuckle, a cotter joint, a bolted, joint, a screw joint, or a universal joint. The first joint 1212, second joint 1220, and/or third joint 1228 may be articulated manually and/or by any actuating technology (e.g., as described herein). The first joint 1212, second joint 1220, and/or third joint 1228 facilitates rotation around an axis independent from each other. Therefore, the emission module 1224 is positionable via multiple degrees of freedom relative to the base 1204.

In some embodiments the disinfection system 1200 may contain one or more sensors 1232 configured to detect movement or the presence of a person. The one or more sensors 1232 may include any sensor technology described herein (e.g., motion sensors, heat sensors). For example, multiple sensors 1232 may be attached to different sides or surfaces of the base 1204. For instance, the multiple sensors 1232 may be arranged in a redundant and/or overlapping manner so that a passenger will be detected even if a single sensor 1232 malfunctions or is blocked.

Figure 13:
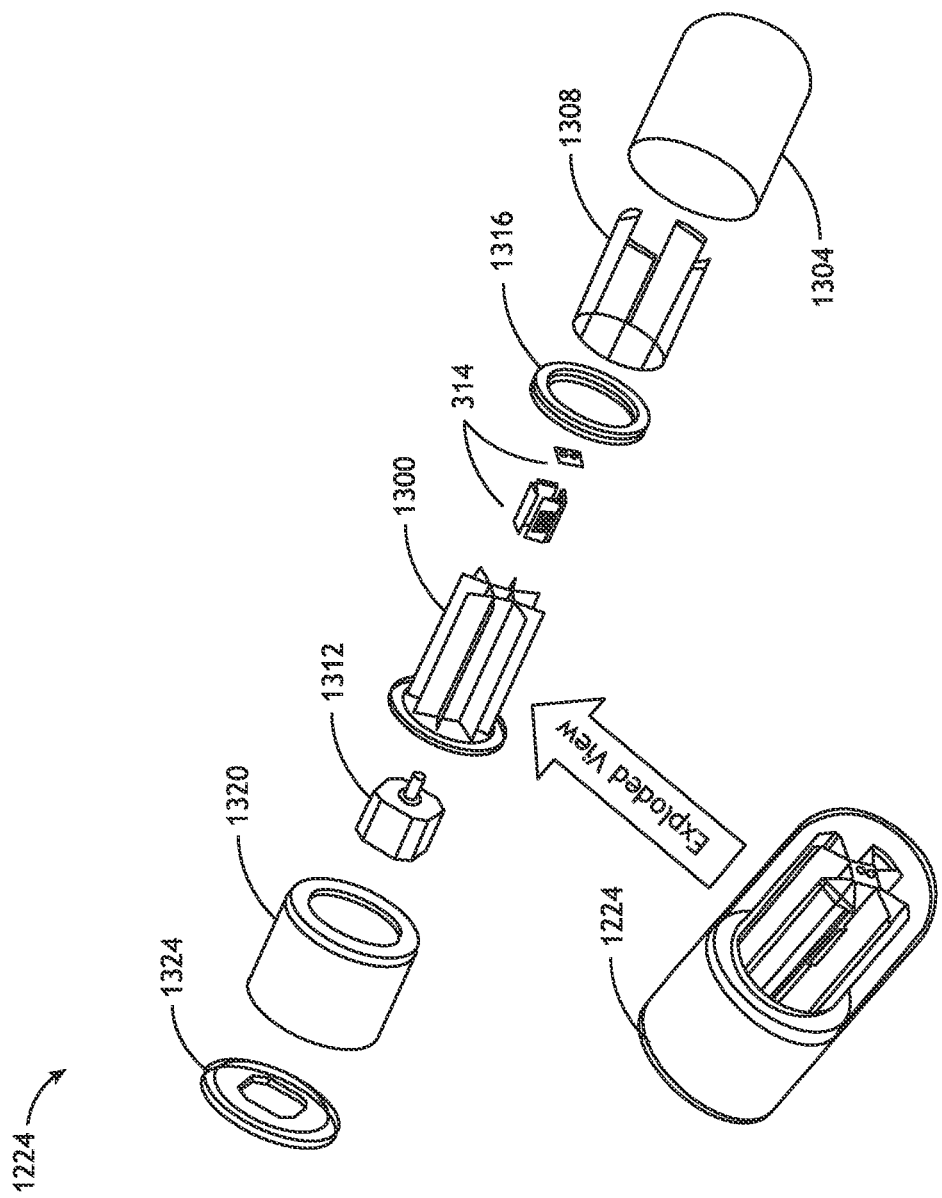
FIG. 13 is a diagram illustrating an exploded view of the emission module, in accordance with one or more embodiments of the disclosure.

FIG. 13 is a diagram illustrating an exploded view of the emission module 1224, in accordance with one or more embodiments of the disclosure. The emission module 1224 includes a light source 1300 containing one or more scanners 314 (e.g., ultraviolet diodes). The light source 1300 may be configured with any number of scanners 314, any configuration of scanners, and within any structural complement (e.g., walls that constrict and/or focus the light from each scanner 314. For example, the light source 1300 may be configured as a four-quadrant scanner. The emission module 1224 may further include a transparent cap 1304, a lens frame 1308 with focusing lenses, a motor 1312 (e.g., rotary actuator) configured to rotate the lens frame 1308 and/or light source 1300 along a cylindrical axis, a bearing 1316 configured to support rotation of the light source 1300 and/or light source 1300 along the cylindrical axis, a housing 1320 and a back plate 1324 configured to house and protect emission module componentry.

Figure 14A:
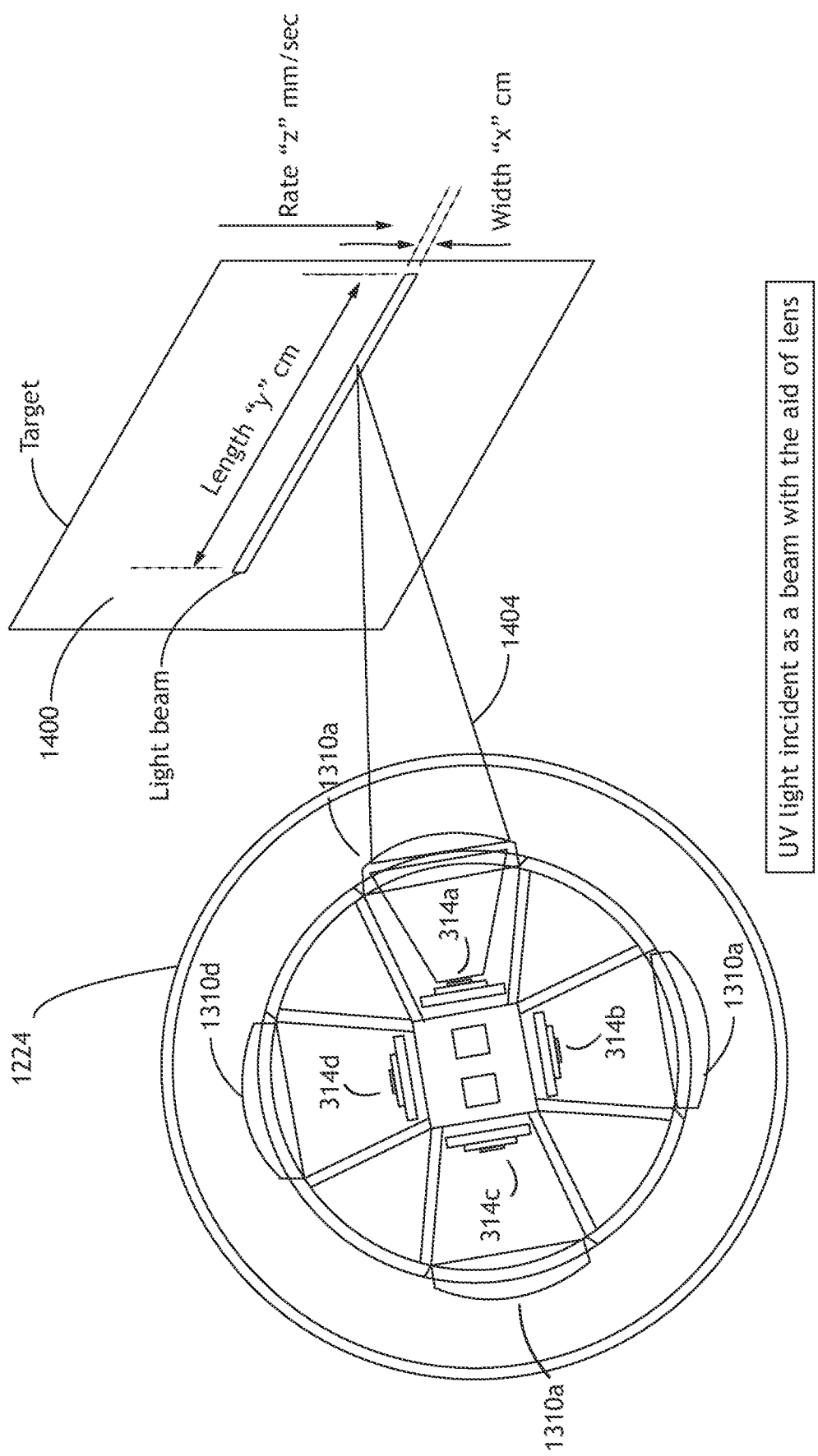
FIG. 14A is a diagram illustrating a close-up view of a face of the emission module and the emission of focused ultraviolet light onto a first surface, in accordance with one or more embodiments of the disclosure.

FIG. 14A is a diagram illustrating a close-up view of a face of the emission module 1224 and the emission of focused ultraviolet light on a first surface 1400, in accordance with one or more embodiments of the disclosure. The first surface 1400 may be configured or defined as the scanning area intended to be scanned by the disinfection system 100, 1100. For example, as shown in FIG. 14, one of the scanners 314a-d (e.g., scanner 314a) is activated, and the focusing lens 1310a is positioned immediately adjacent to the scanner 314a, resulting in an emission of a focused light beam 1404 to a point upon the first surface 1400. The actuators and motor 1312 within the disinfection system 100 may further work in concert to guide the focused light beam 1404 along the X and Y axis of the first surface 1400, resulting in a scanning of the entire first surface 1400. This narrow beam mode of scanning may be referred to as a first scan mode, which may be used in the presence of nearby passengers, as the narrow beam in incident and may be prevented from falling upon a passenger. First scan mode may also be used to disinfect specific components including but not limited to door panels, passenger seats 104, aisles, storage compartments. The power of the light beam 1404 at the first surface 1400 and/or the speed of the light beam traveling along the first surface 1400 may be adjusted to ensure that the scanning of the first surface 1400 results in a sterilization of microbes residing on the first surface 1400. Scanning of the first surface 1400 by the disinfection system 100, 1100 may be performed via any emission module 1224 parameter including but not limited to number of active scanners 314, focused size of the beam, speed of scanning, intensity of the beam, number of beam pulses, and number of repeated scans of the same area of the first surface.

Figure 14B:
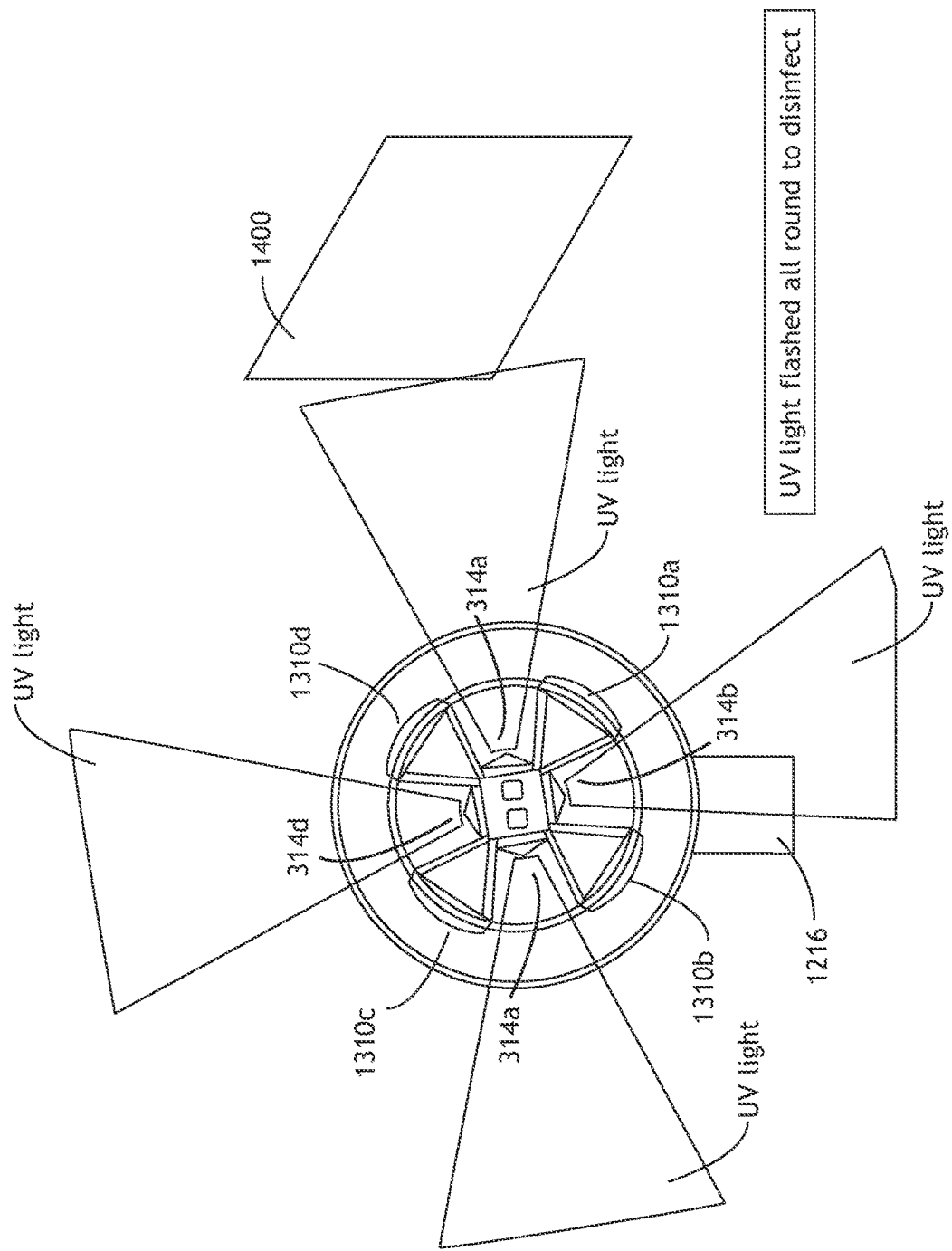
FIG. 14B is a diagram illustrating a close-up view of a face of the emission module and the broad emission of ultraviolet light on a first surface, in accordance with one or more embodiments of the disclosure.

FIG. 14B is a diagram illustrating a close-up view of a face of the emission module 1224 and the broad emission of ultraviolet light on a first surface 1400, in accordance with one or more embodiments of the disclosure. As compared to FIG. 14A, the lens frame 1308 has been rotated relative to the light source 1300, resulting is ultraviolet light emitted by the scanners 314a-d that are no longer focused through the focusing lenses 1310a-d, resulting in the emission of broad beams of ultraviolet light. The broad beam application, of ultraviolet light, referred to as a second scan mode, enables whole portions of the first surface 1400 to be exposed to ultraviolet light at the same time. While the intensity of ultraviolet light on the first surface 1400 is lower than that of the focused light beam 1404, the time that the broad beam may be applied to the first surface 1400 may be increased, ensuring the sterilization of microbes. In comparison of the two scan modes, alignment of the focusing lens 1310 with one of the one or more scanners 314 via the motor 1312, results in electromagnetic energy (e.g., ultraviolet light) emitted from one or more scanners 314 as a narrowly focused beam, whereas a nonalignment of the focusing lens 1310 with one of the one or more scanners 314 (e.g., a positioning of the focusing lens 1310 out of alignment with the one of the one or more scanners 314) via the motor 1312, results in electromagnetic energy (e.g., ultraviolet light) emitted from one or more scanners 314 as a broadly focused beam.

Figure 15:
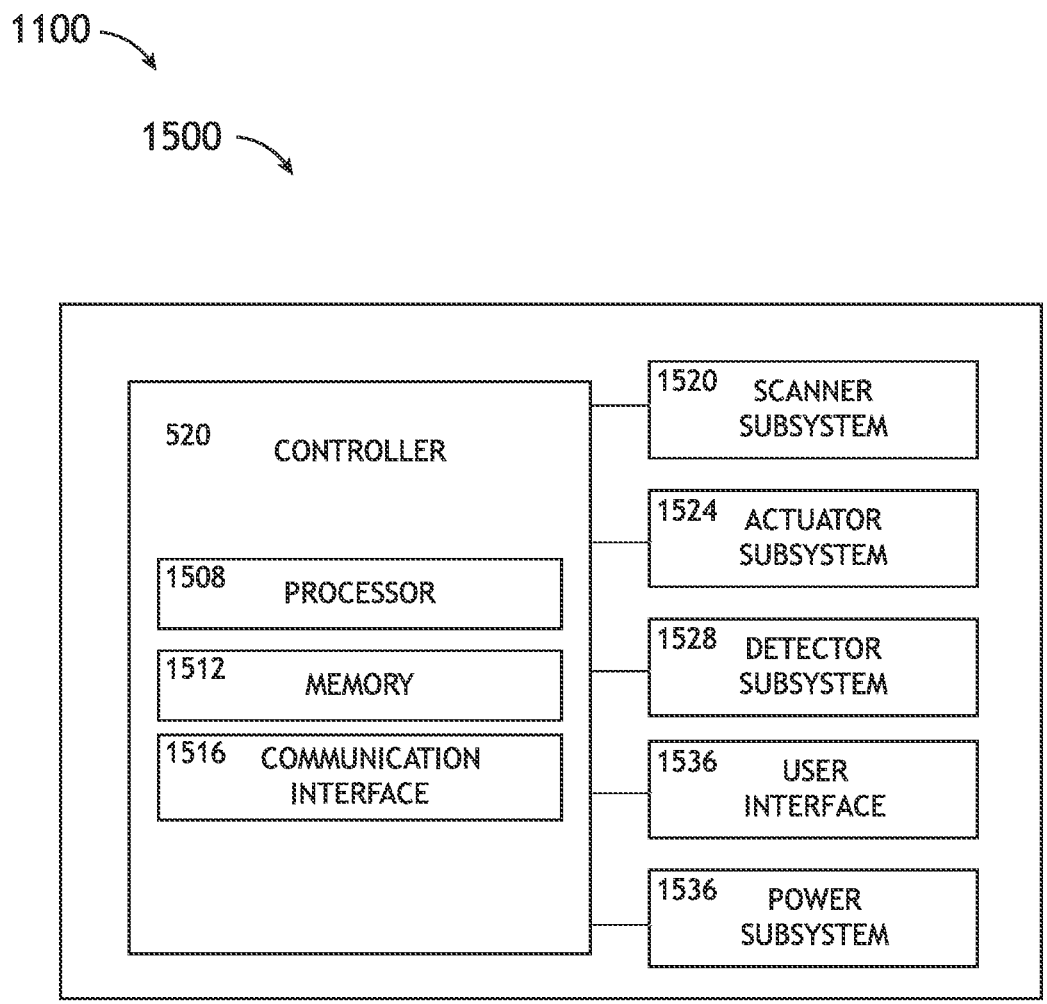
FIG. 15 is a block diagram illustrating a control system of the disinfection system, in accordance with one or more embodiments of the disclosure.

FIG. 15 is a block diagram illustrating a control system 1500 of the disinfection system 1200, in accordance with one or more embodiments of the disclosure. The control system 1500 may include one or more, or all, components of the control system 1000, or vice versa. For example, the control system 1500 includes a controller 1504 configured similarly to controller 508 that further includes one or more processors 1508, a memory 1512, and a communication interface 1516 configured similarly to that of the one or more processors 1002, memory 1004, and communication interface 1008, respectively. The control system further includes a scanner subsystem 1520, an actuator subsystem 1524, a sensor subsystem 1528, a user interface 1532, and a power subsystem 1536 configured similarly to that of the scanner subsystem 1012, the actuator subsystem 1016, the sensor subsystem 1020, the user interface 1024, and the power subsystem 1028, respectively.

Figure 16:
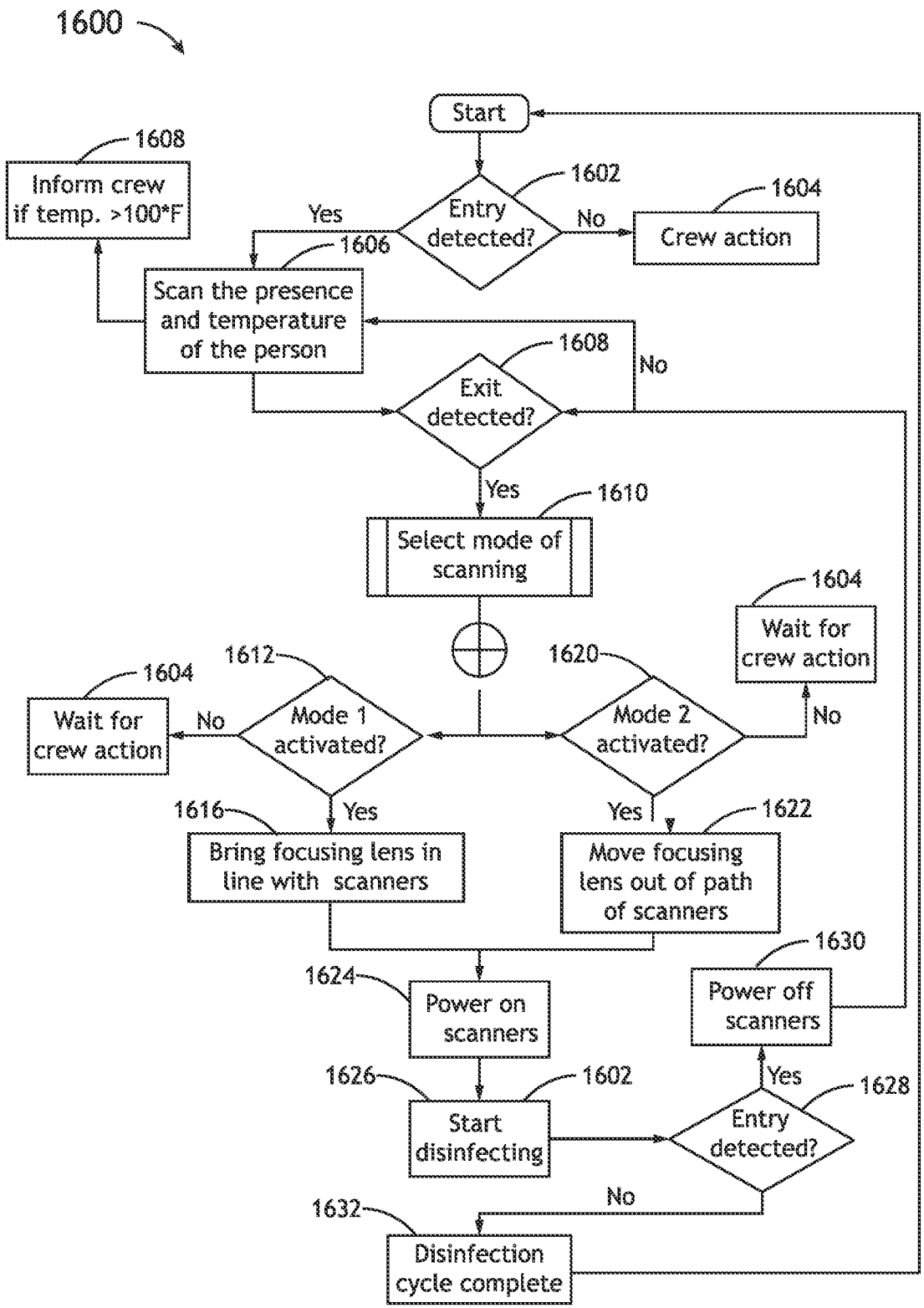
FIG. 16 is a flow chart illustrating a method of operating the disinfection system, in accordance with one or more embodiments of the disclosure.

FIG. 16 is a flow chart illustrating a method 1600 of operating the disinfection system 1200, in accordance with one or more embodiments of the disclosure. The method 1600 may include one or more, or all the steps of method 1100, and vice versa. Once the disinfection system 1200 is powered on, a step 1602 of determining the presence or absence of a person in the area to be scanned is performed (e.g., via the one or more sensors 504). For example, a disinfection system 1200 may utilize a motion detector to determine the presence or absence of a passenger. If no presence of a person is detected, the method may progress to a step 1604 of informing a crew member. Once informed, the crew member may visually check to ensure the absence of a person within the area to be scanned and/or initiate the sterilization protocol. If motion is detected within the area to be scanned, the method 1600 may progress to a next step 1606 of scanning and/or rescanning the presence of the person in the area to be scanned. For example, the step 1606 may include the use of a heat sensor to detect the presence of a person. The method 1600 may also include a step 1608 of informing a crew member if a person has a high temperature. For instance, the disinfection system 1200 may alert a crew member if the measured temperature of a person is above a predetermined fever threshold, indicating that the person may be sick and potentially contagious. The disinfection system 1200 may then perform and/or repeat a step 1608 of determining if a person has exited the area to be scanned (e.g., via the one or more sensors 504)

Once the disinfection system 1200 has determined that no person is in the area to be scanned, the disinfection system 1200 may then perform a step 1610 of selecting a mode of scanning. For example, the disinfection system 1200 may include a step 1612 of activating the first scan mode and a step 1616 of bringing the focusing lens 1310 in line with the scanners 314. Alternatively, the disinfection system may include a step 1620 of activating the second scan mode and a step 1622 of moving the focusing lens 1310 out of the path of the scanners 314. The method 1600 may then proceed with a step 1624 of powering of the scanners 314 and a step 1626 of initiating the disinfection protocol.

Once the disinfection protocol has been initiated, the disinfection system 1200 may perform and/or repeat a step 1628 of determining if a person has entered the area to be scanned (e.g., via the one or more sensors 504). If a person is detected within the area to be scanned, the method may proceed to a step 1630 of powering off of the diodes the proceeding to the step of 1608 to detect if the person has left the area to be scanned. It is important to turn off ultraviolet scanning equipment, as brief exposure to ultraviolet light may damage skin and retinal tissue. If a person is not detected, the method may proceed with a step 1632 of completing the disinfection protocol.

Figure 17A:
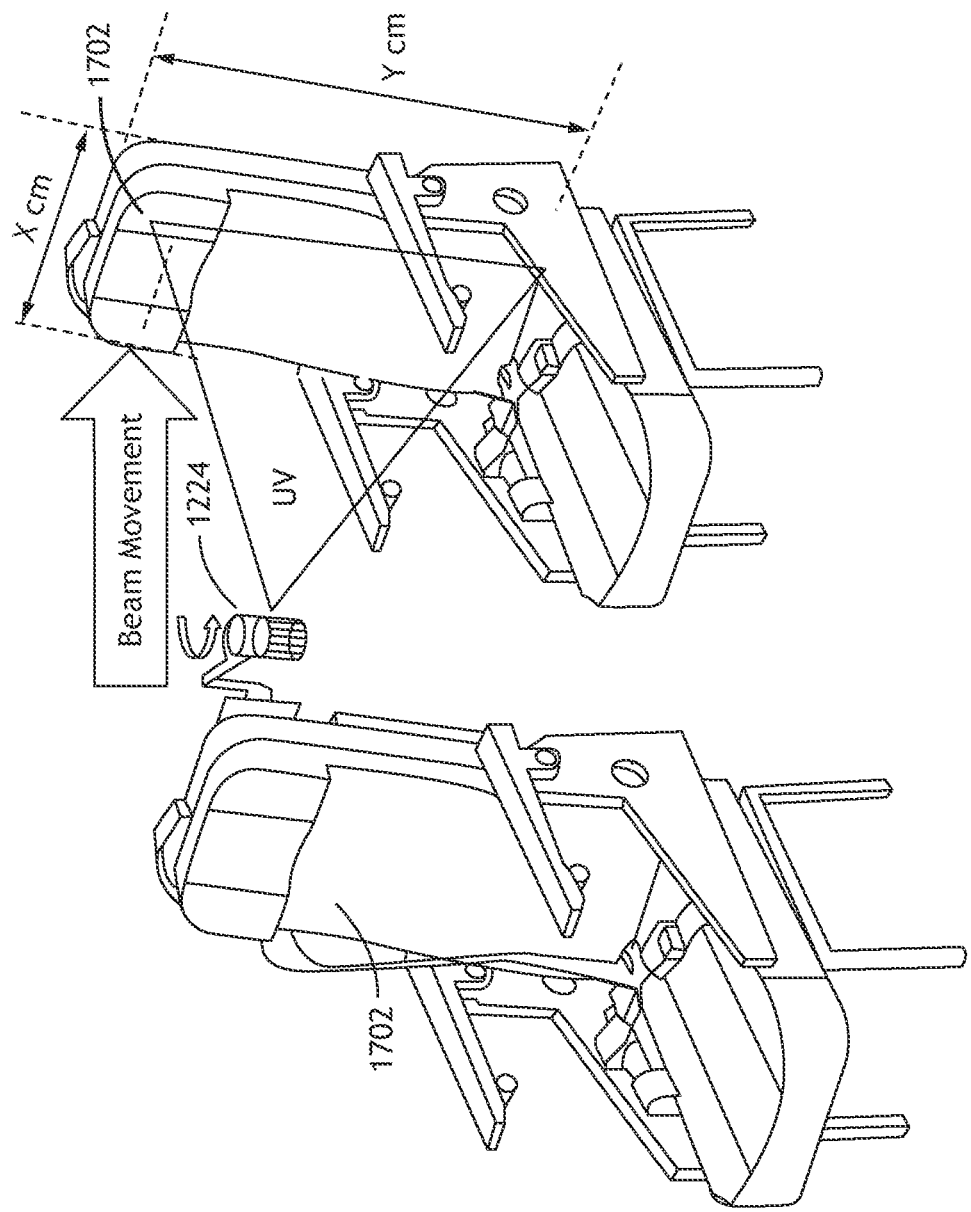
FIG. 17A is a drawing illustrating a disinfection system attached to the back of a forward passenger seat and scanning a rearward passenger seat, in accordance with one or more embodiments of the disclosure.
Figure 17B:
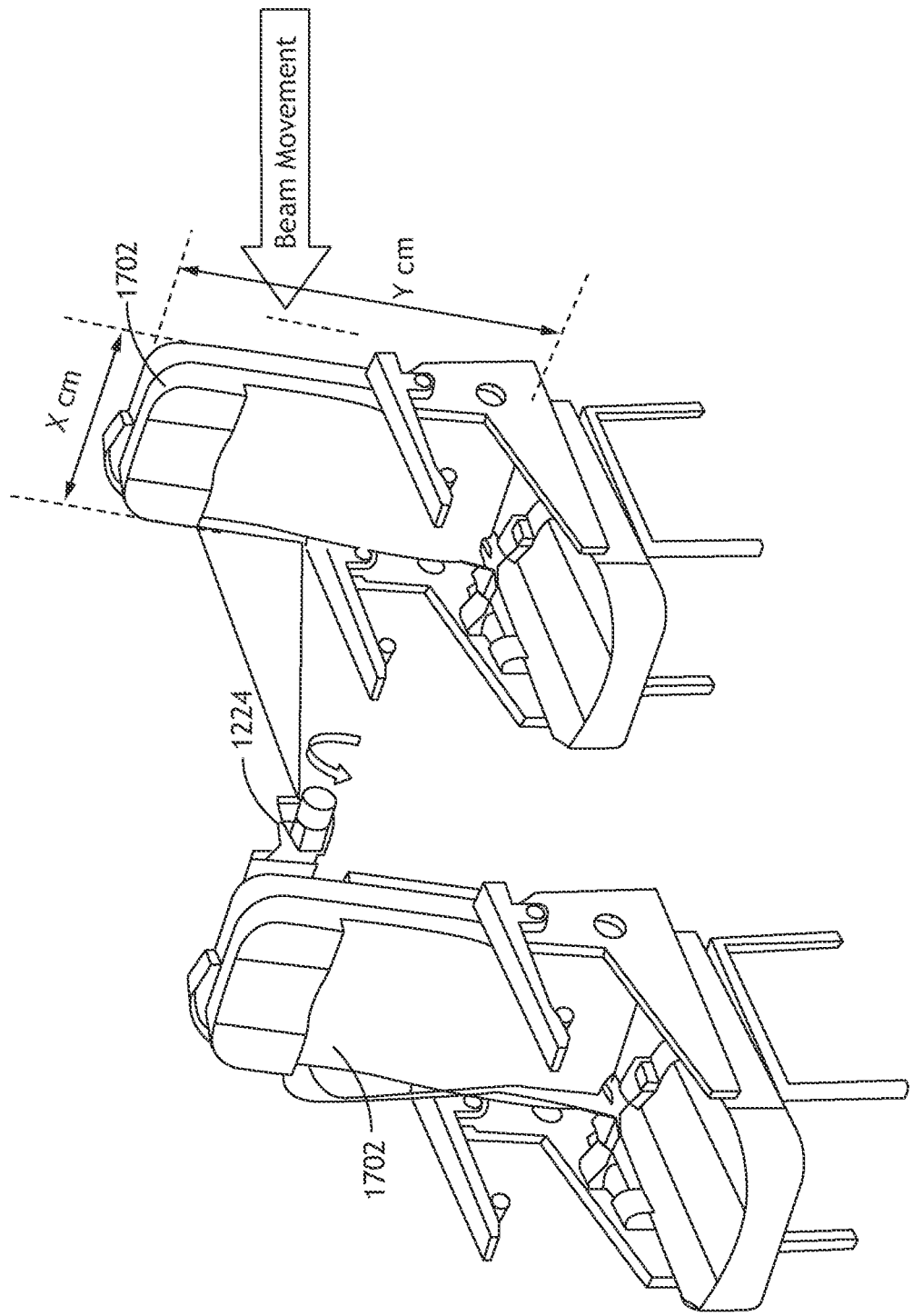
FIG. 17B is a drawing illustrating a disinfection system attached to the back of a forward passenger seat and scanning a rearward passenger seat, in accordance with one or more embodiments of the disclosure.

FIGS. 17A and 17B are drawings illustrating a disinfection system 1200 attached to the back of a forward passenger seat 1702 and scanning a rearward passenger seat 1704, in accordance with one or more embodiments of the disclosure. For example, the emission module 1224 may be configured to emit a broad beam of ultraviolet light along an X-axis via the rotation of the light source 1300 and/or the focusing lens 1310 (e.g., as in FIG. 17A). In another example, the emission module 1224 may be configured to emit a broad beam of ultraviolet light along a Y-axis via the rotation of the light source 1300 and/or the focusing lens 1310 (e.g., as in FIG. 17B).

It is to be understood that embodiments of the methods disclosed herein may include one or more of the steps described herein. Further, such steps may be carried out in any desired order and two or more of the steps may be carried out simultaneously with one another. Two or more of the steps disclosed herein may be combined in a single step, and in some embodiments, one or more of the steps may be carried out as two or more sub-steps. Further, other steps or sub-steps may be carried in addition to, or as substitutes to one or more of the steps disclosed herein.

Although inventive concepts have been described with reference to the embodiments illustrated in the attached drawing figures, equivalents may be employed and substitutions made herein without departing from the scope of the claims. Components illustrated and described herein are merely examples of a system/device and components that may be used to implement embodiments of the inventive concepts and may be replaced with other devices and components without departing from the scope of the claims. Furthermore, any dimensions, degrees, and/or numerical ranges provided herein are to be understood as non-limiting examples unless otherwise specified in the claims.

What is claimed is:

1. A disinfection system comprising:
   a base, wherein the base includes one or more track grooves and one or more pinion gears;
   a rail slidably coupled to the base, wherein the one or more track grooves receive the rail, wherein the rail is attached to an interior surface of an aircraft cabin to slidably translate the base along the rail of the interior surface of the aircraft cabin;
   a first arm mechanically coupled to the base at a first joint, wherein the first arm is configured to rotate along a first axis;
   a second arm mechanically coupled to the first arm at a second joint, wherein the second arm is configured to rotate along a second axis;
   an emission module mechanically coupled via a swivel block to the second arm at a third joint and configured to rotate along a third axis, the emission module comprising at least one third arm coupled to the swivel block at a fourth joint and configured to rotate along a fourth axis, wherein the at least one third arm comprises at least a first section and a second section, wherein the first section telescopes within the second section, wherein both the first section and the second section include one or more scanners configured to emit electromagnetic energy upon a first surface, wherein the electromagnetic energy disinfects the first surface;
   a sensor coupled to the base, wherein the sensor is configured to detect a presence of a person at the first surface throughout the interior surface of the aircraft cabin as the base slidably translates along the rail;
   a first actuator operationally coupled to at least one of the first arm, the second arm, or the emission module; and
   a controller communicatively coupled to the emission module, the one or more scanners, and the first actuator, wherein the controller comprises:
   at least one processor; and
   a memory coupled to the at least one processor, the memory having instructions stored upon that, when executed by the at least one processor, cause the controller to:
   determine an absence of a person adjacent to the first surface;
   activate at least one scanner of the one or more scanners; and
   focus the electromagnetic energy on the first surface.

2. The disinfection system of claim 1, wherein the second arm is configured as a second telescopic arm.

3. The disinfection system of claim 2, wherein the second telescopic arm is configured to rotate along a cylindrical axis.

4. The disinfection system of claim 1, wherein the third arm is configured to rotate along a cylindrical axis.

5. The disinfection system of claim 1, wherein the electromagnetic energy is configured as at least one of ultraviolet light or infrared light.

6. The disinfection system of claim 1, wherein the sensor is configured as a motion sensor.

7. The disinfection system of claim 1, wherein the sensor is configured as a heat sensor.

8. The disinfection system of claim 1, wherein the base further comprises one or more additional scanners.

\* \* \* \* \*